US011797087B2

(12) United States Patent
Barachant

(10) Patent No.: US 11,797,087 B2
(45) Date of Patent: Oct. 24, 2023

(54) METHODS AND APPARATUS FOR AUTOCALIBRATION OF A WEARABLE ELECTRODE SENSOR SYSTEM

(71) Applicant: META PLATFORMS TECHNOLOGIES, LLC, Menlo Park, CA (US)

(72) Inventor: Alexandre Barachant, New York, NY (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 17/297,449

(22) PCT Filed: Nov. 27, 2019

(86) PCT No.: PCT/US2019/063587
§ 371 (c)(1),
(2) Date: May 26, 2021

(87) PCT Pub. No.: WO2020/112986
PCT Pub. Date: Jun. 4, 2020

(65) Prior Publication Data
US 2021/0397256 A1 Dec. 23, 2021

Related U.S. Application Data

(60) Provisional application No. 62/771,957, filed on Nov. 27, 2018.

(51) Int. Cl.
*G06F 3/01* (2006.01)
*A61B 5/397* (2021.01)
(Continued)

(52) U.S. Cl.
CPC .............. *G06F 3/015* (2013.01); *A61B 5/067* (2013.01); *A61B 5/397* (2021.01); *A61B 5/6824* (2013.01);
(Continued)

(58) Field of Classification Search
CPC ........ G06F 3/015; G06F 3/017; G06F 3/0346; G06F 3/011; G06F 3/014; A61B 5/067;
(Continued)

(56) References Cited

U.S. PATENT DOCUMENTS

| 1,411,995 A | 4/1922 | Dull |
| 3,408,133 A | 10/1968 | Lee |

(Continued)

FOREIGN PATENT DOCUMENTS

| CA | 2902045 A1 | 8/2014 |
| CA | 2921954 A1 | 2/2015 |

(Continued)

OTHER PUBLICATIONS

International Preliminary Report on Patentability for International Application No. PCT/US2019/063587, dated Jun. 10, 2021, 13 pages.

(Continued)

*Primary Examiner* — David D Davis
(74) *Attorney, Agent, or Firm* — Greenberg Traurig, LLP

(57) ABSTRACT

Methods and systems used in calibrating the position and/or orientation of a wearable device configured to be worn on a wrist or forearm of a user, the method comprises sensing a plurality of neuromuscular signals from the user using a plurality of sensors arranged on the wearable device, and providing the plurality of neuromuscular signals and/or signals derived from the plurality of neuromuscular signals as inputs to one or more trained autocalibration models, determining based, at least in part, on the output of the one (Continued)

or more trained autocalibration models, a current position and/or orientation of the wearable device on the user, and generating a control signal based, at least in part, on the current position and/or orientation of the wearable device on the user and the plurality of neuromuscular signals.

37 Claims, 10 Drawing Sheets

(51) Int. Cl.
    *A61B 5/06*            (2006.01)
    *A61B 5/00*            (2006.01)
    *G06F 3/0346*         (2013.01)
    *G06N 3/04*            (2023.01)

(52) U.S. Cl.
    CPC ............ *A61B 5/7221* (2013.01); *G06F 3/017* (2013.01); *G06F 3/0346* (2013.01); *G06N 3/04* (2013.01); *A61B 2560/0223* (2013.01)

(58) Field of Classification Search
    CPC ..... A61B 5/397; A61B 5/6824; A61B 5/7221; A61B 2560/0223; A61B 5/06; A61B 5/24; A61B 5/389; A61B 2560/0238; A61B 5/7267; G06N 3/04
    See application file for complete search history.

(56) References Cited

U.S. PATENT DOCUMENTS

| | | | |
|---|---|---|---|
| 3,580,243 A | 5/1971 | Johnson | |
| 3,620,208 A | 11/1971 | Wayne et al. | |
| 3,712,716 A | 1/1973 | Cornsweet et al. | |
| 3,735,425 A | 5/1973 | Hoshall et al. | |
| 3,880,146 A | 4/1975 | Everett et al. | |
| 4,055,168 A | 10/1977 | Miller et al. | |
| 4,602,639 A | 7/1986 | Hoogendoorn et al. | |
| 4,705,408 A | 11/1987 | Jordi | |
| 4,817,064 A | 3/1989 | Milles | |
| 4,896,120 A | 1/1990 | Kamil | |
| 4,978,213 A | 12/1990 | El Hage | |
| 5,003,978 A | 4/1991 | Dunseath, Jr. | |
| D322,227 S | 12/1991 | Warhol | |
| 5,081,852 A | 1/1992 | Cox | |
| 5,103,323 A | 4/1992 | Magarinos et al. | |
| 5,231,674 A | 7/1993 | Cleveland et al. | |
| 5,251,189 A | 10/1993 | Thorp | |
| D348,660 S | 7/1994 | Parsons | |
| 5,445,869 A | 8/1995 | Ishikawa et al. | |
| 5,462,065 A | 10/1995 | Cusimano | |
| 5,467,104 A | 11/1995 | Furness, III et al. | |
| 5,482,051 A | 1/1996 | Reddy et al. | |
| 5,589,956 A | 12/1996 | Morishima et al. | |
| 5,596,339 A | 1/1997 | Furness, III et al. | |
| 5,605,059 A | 2/1997 | Woodward | |
| 5,625,577 A | 4/1997 | Kunii et al. | |
| 5,683,404 A | 11/1997 | Johnson | |
| 5,742,421 A | 4/1998 | Wells et al. | |
| 6,005,548 A | 12/1999 | Latypov et al. | |
| 6,008,781 A | 12/1999 | Furness, III et al. | |
| 6,009,210 A | 12/1999 | Kang | |
| 6,027,216 A | 2/2000 | Guyton et al. | |
| 6,032,530 A | 3/2000 | Hock | |
| D422,617 S | 4/2000 | Simioni | |
| 6,066,794 A | 5/2000 | Longo | |
| 6,184,847 B1 | 2/2001 | Fateh et al. | |
| 6,236,476 B1 | 5/2001 | Son et al. | |
| 6,238,338 B1 | 5/2001 | DeLuca et al. | |
| 6,244,873 B1 | 6/2001 | Hill et al. | |
| 6,317,103 B1 | 11/2001 | Furness, III et al. | |
| 6,377,277 B1 | 4/2002 | Yamamoto | |
| D459,352 S | 6/2002 | Giovanniello | |
| 6,411,843 B1 | 6/2002 | Zarychta | |
| 6,487,906 B1 | 12/2002 | Hock | |
| 6,510,333 B1 | 1/2003 | Licata et al. | |
| 6,527,711 B1 | 3/2003 | Stivoric et al. | |
| 6,619,836 B1 | 9/2003 | Silvant et al. | |
| 6,639,570 B2 | 10/2003 | Furness, III et al. | |
| 6,658,287 B1 | 12/2003 | Litt et al. | |
| 6,720,984 B1 | 4/2004 | Jorgensen et al. | |
| 6,743,982 B2 | 6/2004 | Biegelsen et al. | |
| 6,771,294 B1 | 8/2004 | Pulli et al. | |
| 6,774,885 B1 | 8/2004 | Even-Zohar | |
| 6,807,438 B1 | 10/2004 | Brun Del Re et al. | |
| D502,661 S | 3/2005 | Rapport | |
| D502,662 S | 3/2005 | Rapport | |
| 6,865,409 B2 | 3/2005 | Getsla et al. | |
| D503,646 S | 4/2005 | Rapport | |
| 6,880,364 B1 | 4/2005 | Vidolin et al. | |
| 6,901,286 B1 | 5/2005 | Sinderby et al. | |
| 6,927,343 B2 | 8/2005 | Watanabe et al. | |
| 6,942,621 B2 | 9/2005 | Avinash et al. | |
| 6,965,842 B2 | 11/2005 | Rekimoto | |
| 6,972,734 B1 | 12/2005 | Ohshima et al. | |
| 6,984,208 B2 | 1/2006 | Zheng | |
| 7,022,919 B2 | 4/2006 | Brist et al. | |
| 7,028,507 B2 | 4/2006 | Rapport | |
| 7,086,218 B1 | 8/2006 | Pasach | |
| 7,089,148 B1 | 8/2006 | Bachmann et al. | |
| D535,401 S | 1/2007 | Travis et al. | |
| 7,173,437 B2 | 2/2007 | Hervieux et al. | |
| 7,209,114 B2 | 4/2007 | Radley-Smith | |
| D543,212 S | 5/2007 | Marks | |
| 7,265,298 B2 | 9/2007 | Maghribi et al. | |
| 7,271,774 B2 | 9/2007 | Puuri | |
| 7,333,090 B2 | 2/2008 | Tanaka et al. | |
| 7,351,975 B2 | 4/2008 | Brady et al. | |
| 7,450,107 B2 | 11/2008 | Radley-Smith | |
| 7,473,888 B2 | 1/2009 | Wine et al. | |
| 7,491,892 B2 | 2/2009 | Wagner et al. | |
| 7,517,725 B2 | 4/2009 | Reis | |
| 7,558,622 B2 | 7/2009 | Tran | |
| 7,574,253 B2 | 8/2009 | Edney et al. | |
| 7,580,742 B2 | 8/2009 | Tan et al. | |
| 7,596,393 B2 | 9/2009 | Jung et al. | |
| 7,618,260 B2 | 11/2009 | Daniel et al. | |
| 7,636,549 B2 | 12/2009 | Ma et al. | |
| 7,640,007 B2 | 12/2009 | Chen et al. | |
| 7,660,126 B2 | 2/2010 | Cho et al. | |
| 7,684,105 B2 | 3/2010 | Lamontagne et al. | |
| 7,747,113 B2 | 6/2010 | Mukawa et al. | |
| 7,761,390 B2 | 7/2010 | Ford | |
| 7,773,111 B2 | 8/2010 | Cleveland et al. | |
| 7,787,946 B2 | 8/2010 | Stahmann et al. | |
| 7,805,386 B2 | 9/2010 | Greer | |
| 7,809,435 B1 | 10/2010 | Ettare et al. | |
| 7,844,310 B2 | 11/2010 | Anderson | |
| D628,616 S | 12/2010 | Yuan | |
| 7,850,306 B2 | 12/2010 | Uusitalo et al. | |
| 7,870,211 B2 | 1/2011 | Pascal et al. | |
| D633,939 S | 3/2011 | Puentes et al. | |
| D634,771 S | 3/2011 | Fuchs | |
| 7,901,368 B2 | 3/2011 | Flaherty et al. | |
| 7,925,100 B2 | 4/2011 | Howell et al. | |
| 7,948,763 B2 | 5/2011 | Chuang | |
| D640,314 S | 6/2011 | Yang | |
| D643,428 S | 8/2011 | Janky et al. | |
| D646,192 S | 10/2011 | Woode | |
| D649,177 S | 11/2011 | Cho et al. | |
| 8,054,061 B2 | 11/2011 | Prance et al. | |
| D654,622 S | 2/2012 | Hsu | |
| 8,120,828 B2 | 2/2012 | Schwerdtner | |
| 8,170,656 B2 * | 5/2012 | Tan .................. G06F 3/017 | |
| | | | 345/157 |
| 8,179,604 B1 | 5/2012 | Prada Gomez et al. | |
| 8,188,937 B1 | 5/2012 | Amafuji et al. | |
| 8,190,249 B1 | 5/2012 | Gharieb et al. | |
| D661,613 S | 6/2012 | Demeglio | |
| 8,203,502 B1 | 6/2012 | Chi et al. | |
| 8,207,473 B2 | 6/2012 | Axisa et al. | |
| 8,212,859 B2 | 7/2012 | Tang et al. | |
| D667,482 S | 9/2012 | Healy et al. | |

(56) References Cited

U.S. PATENT DOCUMENTS

| | | |
|---|---|---|
| D669,522 S | 10/2012 | Klinar et al. |
| D669,523 S | 10/2012 | Wakata et al. |
| D671,590 S | 11/2012 | Klinar et al. |
| 8,311,623 B2 | 11/2012 | Sanger |
| 8,348,538 B2 | 1/2013 | Van Loenen et al. |
| 8,351,651 B2 | 1/2013 | Lee |
| 8,355,671 B2 | 1/2013 | Kramer et al. |
| 8,384,683 B2 | 2/2013 | Luo |
| 8,386,025 B2 | 2/2013 | Hoppe |
| 8,389,862 B2 | 3/2013 | Arora et al. |
| 8,421,634 B2 | 4/2013 | Tan et al. |
| 8,427,977 B2 | 4/2013 | Workman et al. |
| D682,343 S | 5/2013 | Waters |
| D682,727 S | 5/2013 | Bulgari |
| 8,435,191 B2 | 5/2013 | Barboutis et al. |
| 8,437,844 B2 | 5/2013 | Syed Momen et al. |
| 8,447,704 B2 | 5/2013 | Tan et al. |
| D685,019 S | 6/2013 | Li |
| 8,467,270 B2 | 6/2013 | Gossweiler, III et al. |
| 8,469,741 B2 | 6/2013 | Oster et al. |
| D687,087 S | 7/2013 | Iurilli |
| 8,484,022 B1 | 7/2013 | Vanhoucke |
| D689,862 S | 9/2013 | Liu |
| D692,941 S | 11/2013 | Klinar et al. |
| 8,591,411 B2 | 11/2013 | Banet et al. |
| D695,333 S | 12/2013 | Farnam et al. |
| D695,454 S | 12/2013 | Moore |
| 8,620,361 B2 | 12/2013 | Bailey et al. |
| 8,624,124 B2 | 1/2014 | Koo et al. |
| 8,634,119 B2 | 1/2014 | Bablumyan et al. |
| D701,555 S | 3/2014 | Markovitz et al. |
| 8,666,212 B1 | 3/2014 | Amirparviz |
| 8,702,629 B2 | 4/2014 | Giuffrida et al. |
| 8,704,882 B2 | 4/2014 | Turner |
| D704,248 S | 5/2014 | Dichiara |
| 8,718,980 B2 | 5/2014 | Garudadri et al. |
| 8,743,052 B1 | 6/2014 | Keller et al. |
| 8,744,543 B2 | 6/2014 | Li et al. |
| 8,754,862 B2 | 6/2014 | Zaliva |
| 8,777,668 B2 | 7/2014 | Ikeda et al. |
| D716,457 S | 10/2014 | Brefka et al. |
| D717,685 S | 11/2014 | Bailey et al. |
| 8,879,276 B2 | 11/2014 | Wang |
| 8,880,163 B2 | 11/2014 | Barachant et al. |
| 8,883,287 B2 | 11/2014 | Boyce et al. |
| 8,890,875 B2 | 11/2014 | Jammes et al. |
| 8,892,479 B2 | 11/2014 | Tan et al. |
| 8,895,865 B2 | 11/2014 | Lenahan et al. |
| D719,568 S | 12/2014 | Heinrich et al. |
| D719,570 S | 12/2014 | Heinrich et al. |
| 8,912,094 B2 | 12/2014 | Koo et al. |
| 8,914,472 B1 | 12/2014 | Lee et al. |
| 8,922,481 B1 | 12/2014 | Kauffmann et al. |
| D723,093 S | 2/2015 | Li |
| 8,954,135 B2 | 2/2015 | Yuen et al. |
| D724,647 S | 3/2015 | Rohrbach |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,037,530 B2 | 5/2015 | Tan et al. |
| 9,086,687 B2 | 7/2015 | Park et al. |
| 9,092,664 B2 | 7/2015 | Forutanpour et al. |
| D736,664 S | 8/2015 | Paradise et al. |
| 9,107,586 B2 | 8/2015 | Tran |
| D738,373 S | 9/2015 | Davies et al. |
| 9,135,708 B2 | 9/2015 | Ebisawa |
| 9,146,730 B2 | 9/2015 | Lazar |
| D741,855 S | 10/2015 | Park et al. |
| 9,170,674 B2 | 10/2015 | Forutanpour et al. |
| D742,272 S | 11/2015 | Bailey et al. |
| D742,874 S | 11/2015 | Cheng et al. |
| D743,963 S | 11/2015 | Osterhout |
| 9,182,826 B2 | 11/2015 | Powledge et al. |
| 9,211,417 B2 | 12/2015 | Hieldman et al. |
| 9,218,574 B2 | 12/2015 | Phillipps et al. |
| D747,714 S | 1/2016 | Erbeus |
| D747,759 S | 1/2016 | Ho |
| 9,235,934 B2 | 1/2016 | Mandella et al. |
| 9,240,069 B1 | 1/2016 | Li |
| D750,623 S | 3/2016 | Park et al. |
| D751,065 S | 3/2016 | Magi |
| 9,278,453 B2 | 3/2016 | Assad |
| 9,299,248 B2 | 3/2016 | Lake et al. |
| D756,359 S | 5/2016 | Bailey et al. |
| 9,329,694 B2 | 5/2016 | Slonneger |
| 9,341,659 B2 | 5/2016 | Poupyrev et al. |
| 9,349,280 B2 | 5/2016 | Baldwin et al. |
| 9,351,653 B1 | 5/2016 | Harrison |
| D758,476 S | 6/2016 | Ho |
| D760,313 S | 6/2016 | Ho et al. |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,393,418 B2 | 7/2016 | Giuffrida et al. |
| 9,402,582 B1 | 8/2016 | Parviz et al. |
| 9,408,316 B2 | 8/2016 | Bailey et al. |
| 9,418,927 B2 | 8/2016 | Axisa et al. |
| D766,895 S | 9/2016 | Choi |
| 9,439,566 B2 | 9/2016 | Arne et al. |
| D768,627 S | 10/2016 | Rochat et al. |
| 9,459,697 B2 | 10/2016 | Bedikian et al. |
| 9,472,956 B2 | 10/2016 | Michaelis et al. |
| 9,477,313 B2 | 10/2016 | Mistry et al. |
| D771,735 S | 11/2016 | Lee et al. |
| 9,483,123 B2 | 11/2016 | Aleem et al. |
| 9,529,434 B2 | 12/2016 | Choi et al. |
| D780,828 S | 3/2017 | Bonaventura et al. |
| D780,829 S | 3/2017 | Bonaventura et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,652,047 B2 | 5/2017 | Mullins et al. |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,807,221 B2 | 10/2017 | Bailey et al. |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 9,921,641 B1 | 3/2018 | Worley, III et al. |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,185,416 B2 | 1/2019 | Mistry et al. |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,429,928 B2 | 10/2019 | Morun et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 10,520,378 B1 | 12/2019 | Brown et al. |
| 10,528,135 B2 | 1/2020 | Bailey et al. |
| 10,558,273 B2 | 2/2020 | Park et al. |
| 10,592,001 B2 | 3/2020 | Berenzweig et al. |
| 10,610,737 B1 | 4/2020 | Crawford |

(56) References Cited

U.S. PATENT DOCUMENTS

| | | |
|---|---|---|
| 10,676,083 B1 | 6/2020 | De Sapio et al. |
| 10,687,759 B2 | 6/2020 | Guo et al. |
| 10,905,350 B2 | 2/2021 | Berenzweig et al. |
| 10,905,383 B2 | 2/2021 | Barachant |
| 10,937,414 B2 | 3/2021 | Berenzweig et al. |
| 10,990,174 B2 | 4/2021 | Kaifosh et al. |
| 11,009,951 B2 | 5/2021 | Bailey et al. |
| 11,150,730 B1 | 10/2021 | Anderson et al. |
| 2001/0033402 A1 | 10/2001 | Popovich |
| 2002/0003627 A1 | 1/2002 | Rieder |
| 2002/0009972 A1 | 1/2002 | Amento et al. |
| 2002/0030636 A1 | 3/2002 | Richards |
| 2002/0032386 A1 | 3/2002 | Sackner et al. |
| 2002/0077534 A1 | 6/2002 | DuRousseau |
| 2002/0094701 A1 | 7/2002 | Biegelsen et al. |
| 2002/0120415 A1 | 8/2002 | Millott et al. |
| 2002/0120916 A1 | 8/2002 | Snider, Jr. |
| 2002/0198472 A1 | 12/2002 | Kramer |
| 2003/0030595 A1 | 2/2003 | Radley-Smith |
| 2003/0036691 A1 | 2/2003 | Stanaland et al. |
| 2003/0051505 A1 | 3/2003 | Robertson et al. |
| 2003/0144586 A1 | 7/2003 | Tsubata |
| 2003/0144829 A1 | 7/2003 | Geatz et al. |
| 2003/0171921 A1 | 9/2003 | Manabe et al. |
| 2003/0182630 A1 | 9/2003 | Saund et al. |
| 2003/0184544 A1 | 10/2003 | Prudent |
| 2004/0010210 A1 | 1/2004 | Avinash et al. |
| 2004/0024312 A1 | 2/2004 | Zheng |
| 2004/0054273 A1 | 3/2004 | Finneran et al. |
| 2004/0068409 A1 | 4/2004 | Tanaka et al. |
| 2004/0073104 A1 | 4/2004 | Brun Del Re et al. |
| 2004/0080499 A1 | 4/2004 | Lui |
| 2004/0092839 A1 | 5/2004 | Shin et al. |
| 2004/0194500 A1 | 10/2004 | Rapport |
| 2004/0210165 A1 | 10/2004 | Marmaropoulos et al. |
| 2004/0243342 A1 | 12/2004 | Rekimoto |
| 2004/0254617 A1 | 12/2004 | Hemmerling et al. |
| 2005/0005637 A1 | 1/2005 | Rapport |
| 2005/0012715 A1 | 1/2005 | Ford |
| 2005/0070227 A1 | 3/2005 | Shen et al. |
| 2005/0070791 A1 | 3/2005 | Edney et al. |
| 2005/0115561 A1 | 6/2005 | Stahmann et al. |
| 2005/0119701 A1 | 6/2005 | Lauter et al. |
| 2005/0177038 A1 | 8/2005 | Kolpin et al. |
| 2005/0179644 A1 | 8/2005 | Alsio et al. |
| 2006/0018833 A1 | 1/2006 | Murphy et al. |
| 2006/0037359 A1 | 2/2006 | Stinespring |
| 2006/0058699 A1 | 3/2006 | Vitiello et al. |
| 2006/0061544 A1 | 3/2006 | Min et al. |
| 2006/0121958 A1 | 6/2006 | Jung et al. |
| 2006/0129057 A1 | 6/2006 | Maekawa et al. |
| 2006/0132705 A1 | 6/2006 | Li |
| 2006/0149338 A1 | 7/2006 | Flaherty et al. |
| 2006/0211956 A1 | 9/2006 | Sankai |
| 2006/0238707 A1 | 10/2006 | Elvesjo et al. |
| 2007/0009151 A1 | 1/2007 | Pittman et al. |
| 2007/0016265 A1 | 1/2007 | Davoodi et al. |
| 2007/0023662 A1 | 2/2007 | Brady et al. |
| 2007/0078308 A1 | 4/2007 | Daly |
| 2007/0132785 A1 | 6/2007 | Ebersole, Jr. et al. |
| 2007/0148624 A1 | 6/2007 | Nativ |
| 2007/0172797 A1 | 7/2007 | Hada et al. |
| 2007/0177770 A1 | 8/2007 | Derchak et al. |
| 2007/0185697 A1 | 8/2007 | Tan et al. |
| 2007/0256494 A1 | 11/2007 | Nakamura et al. |
| 2007/0276270 A1 | 11/2007 | Tran |
| 2007/0279852 A1 | 12/2007 | Daniel et al. |
| 2007/0285399 A1 | 12/2007 | Lund |
| 2008/0001735 A1 | 1/2008 | Tran |
| 2008/0032638 A1 | 2/2008 | Anderson |
| 2008/0051673 A1 | 2/2008 | Kong et al. |
| 2008/0052643 A1 | 2/2008 | Ike et al. |
| 2008/0058668 A1 | 3/2008 | Seyed Momen et al. |
| 2008/0103639 A1 | 5/2008 | Troy et al. |
| 2008/0103769 A1 | 5/2008 | Schultz et al. |
| 2008/0136775 A1 | 6/2008 | Conant |
| 2008/0152217 A1 | 6/2008 | Greer |
| 2008/0163130 A1 | 7/2008 | Westerman |
| 2008/0214360 A1 | 9/2008 | Stirling et al. |
| 2008/0221487 A1 | 9/2008 | Zohar et al. |
| 2008/0262772 A1 | 10/2008 | Luinge et al. |
| 2008/0278497 A1 | 11/2008 | Jammes et al. |
| 2008/0285805 A1 | 11/2008 | Luinge et al. |
| 2009/0005700 A1 | 1/2009 | Joshi et al. |
| 2009/0007597 A1 | 1/2009 | Hanevold |
| 2009/0027337 A1 | 1/2009 | Hildreth |
| 2009/0031757 A1 | 2/2009 | Harding |
| 2009/0040016 A1 | 2/2009 | Ikeda |
| 2009/0051544 A1 | 2/2009 | Niknejad |
| 2009/0079607 A1 | 3/2009 | Denison et al. |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0085864 A1 | 4/2009 | Kutliroff et al. |
| 2009/0102580 A1 | 4/2009 | Uchaykin |
| 2009/0109241 A1 | 4/2009 | Tsujimoto |
| 2009/0112080 A1 | 4/2009 | Matthews |
| 2009/0124881 A1 | 5/2009 | Rytky |
| 2009/0147004 A1 | 6/2009 | Ramon et al. |
| 2009/0179824 A1 | 7/2009 | Tsujimoto et al. |
| 2009/0189864 A1 | 7/2009 | Walker et al. |
| 2009/0189867 A1 | 7/2009 | Krah et al. |
| 2009/0195497 A1 | 8/2009 | Fitzgerald et al. |
| 2009/0204031 A1 | 8/2009 | McNames et al. |
| 2009/0207464 A1 | 8/2009 | Wiltshire et al. |
| 2009/0209878 A1 | 8/2009 | Sanger |
| 2009/0251407 A1 | 10/2009 | Flake et al. |
| 2009/0258669 A1 | 10/2009 | Nie et al. |
| 2009/0265671 A1 | 10/2009 | Sachs et al. |
| 2009/0318785 A1 | 12/2009 | Ishikawa et al. |
| 2009/0319230 A1 | 12/2009 | Case, Jr. et al. |
| 2009/0322653 A1 | 12/2009 | Putilin et al. |
| 2009/0326406 A1* | 12/2009 | Tan ............... G06F 3/017 341/20 |
| 2009/0327171 A1 | 12/2009 | Tan et al. |
| 2010/0030532 A1 | 2/2010 | Arora et al. |
| 2010/0041974 A1 | 2/2010 | Ting et al. |
| 2010/0063794 A1 | 3/2010 | Hernandez-Rebollar |
| 2010/0066664 A1 | 3/2010 | Son et al. |
| 2010/0106044 A1 | 4/2010 | Linderman |
| 2010/0113910 A1 | 5/2010 | Brauers et al. |
| 2010/0142015 A1 | 6/2010 | Kuwahara et al. |
| 2010/0149073 A1 | 6/2010 | Chaum et al. |
| 2010/0150415 A1 | 6/2010 | Atkinson et al. |
| 2010/0228487 A1 | 9/2010 | Leuthardt et al. |
| 2010/0234696 A1 | 9/2010 | Li et al. |
| 2010/0240981 A1 | 9/2010 | Barboutis et al. |
| 2010/0249635 A1 | 9/2010 | Van Der Reijden |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0306713 A1 | 12/2010 | Geisner et al. |
| 2010/0315266 A1 | 12/2010 | Gunawardana et al. |
| 2010/0317958 A1 | 12/2010 | Beck et al. |
| 2011/0007035 A1 | 1/2011 | Shai |
| 2011/0018754 A1 | 1/2011 | Tojima et al. |
| 2011/0025982 A1 | 2/2011 | Takahashi |
| 2011/0054360 A1 | 3/2011 | Son et al. |
| 2011/0065319 A1 | 3/2011 | Oster et al. |
| 2011/0066381 A1 | 3/2011 | Garudadri et al. |
| 2011/0072510 A1 | 3/2011 | Cheswick |
| 2011/0077484 A1 | 3/2011 | Van Slyke et al. |
| 2011/0082838 A1 | 4/2011 | Niemela |
| 2011/0092826 A1 | 4/2011 | Lee et al. |
| 2011/0119216 A1 | 5/2011 | Wigdor |
| 2011/0133934 A1 | 6/2011 | Tan et al. |
| 2011/0134026 A1 | 6/2011 | Kang et al. |
| 2011/0151974 A1 | 6/2011 | Deaguero |
| 2011/0166434 A1 | 7/2011 | Gargiulo |
| 2011/0172503 A1 | 7/2011 | Knepper et al. |
| 2011/0173204 A1 | 7/2011 | Murillo et al. |
| 2011/0173574 A1 | 7/2011 | Clavin et al. |

(56) References Cited

U.S. PATENT DOCUMENTS

| | | |
|---|---|---|
| 2011/0181527 A1 | 7/2011 | Capela et al. |
| 2011/0205242 A1 | 8/2011 | Friesen |
| 2011/0213278 A1 | 9/2011 | Horak et al. |
| 2011/0221672 A1* | 9/2011 | Osterhout ............... G06Q 30/02 345/156 |
| 2011/0224507 A1 | 9/2011 | Banet et al. |
| 2011/0224556 A1 | 9/2011 | Moon et al. |
| 2011/0224564 A1 | 9/2011 | Moon et al. |
| 2011/0230782 A1 | 9/2011 | Bartol et al. |
| 2011/0248914 A1 | 10/2011 | Sherr |
| 2011/0262002 A1 | 10/2011 | Lee |
| 2011/0270135 A1 | 11/2011 | Dooley et al. |
| 2011/0295100 A1 | 12/2011 | Hegde et al. |
| 2011/0313762 A1 | 12/2011 | Ben-David et al. |
| 2012/0002256 A1 | 1/2012 | Lacoste et al. |
| 2012/0007821 A1 | 1/2012 | Zaliva |
| 2012/0029322 A1 | 2/2012 | Wartena et al. |
| 2012/0051005 A1 | 3/2012 | Vanfleteren et al. |
| 2012/0052268 A1 | 3/2012 | Axisa et al. |
| 2012/0053439 A1 | 3/2012 | Ylostalo et al. |
| 2012/0066163 A1 | 3/2012 | Balls et al. |
| 2012/0071092 A1 | 3/2012 | Pasquero et al. |
| 2012/0071780 A1 | 3/2012 | Barachant et al. |
| 2012/0101357 A1 | 4/2012 | Hoskuldsson et al. |
| 2012/0117514 A1 | 5/2012 | Kim et al. |
| 2012/0139817 A1 | 6/2012 | Freeman |
| 2012/0157789 A1 | 6/2012 | Kangas et al. |
| 2012/0157886 A1 | 6/2012 | Tenn et al. |
| 2012/0165695 A1 | 6/2012 | Kidmose et al. |
| 2012/0182309 A1 | 7/2012 | Griffin et al. |
| 2012/0184838 A1 | 7/2012 | John |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0226130 A1 | 9/2012 | De Graff et al. |
| 2012/0249797 A1 | 10/2012 | Haddick et al. |
| 2012/0265090 A1 | 10/2012 | Fink et al. |
| 2012/0265480 A1 | 10/2012 | Oshima |
| 2012/0275621 A1 | 11/2012 | Elko |
| 2012/0283526 A1 | 11/2012 | Gommesen et al. |
| 2012/0283896 A1 | 11/2012 | Persaud et al. |
| 2012/0293548 A1 | 11/2012 | Perez et al. |
| 2012/0302858 A1 | 11/2012 | Kidmose et al. |
| 2012/0320532 A1 | 12/2012 | Wang |
| 2012/0323521 A1 | 12/2012 | De Foras et al. |
| 2013/0004033 A1 | 1/2013 | Trugenberger |
| 2013/0005303 A1 | 1/2013 | Song et al. |
| 2013/0016292 A1 | 1/2013 | Miao et al. |
| 2013/0016413 A1 | 1/2013 | Saeedi et al. |
| 2013/0020948 A1 | 1/2013 | Han et al. |
| 2013/0027341 A1 | 1/2013 | Mastandrea |
| 2013/0038707 A1 | 2/2013 | Cunningham et al. |
| 2013/0077820 A1 | 3/2013 | Marais et al. |
| 2013/0080794 A1 | 3/2013 | Hsieh |
| 2013/0106686 A1 | 5/2013 | Bennett |
| 2013/0123656 A1 | 5/2013 | Heck |
| 2013/0123666 A1 | 5/2013 | Giuffrida et al. |
| 2013/0127708 A1 | 5/2013 | Jung et al. |
| 2013/0131538 A1 | 5/2013 | Gaw et al. |
| 2013/0135223 A1 | 5/2013 | Shai |
| 2013/0135722 A1 | 5/2013 | Yokoyama |
| 2013/0141375 A1 | 6/2013 | Ludwig et al. |
| 2013/0144629 A1 | 6/2013 | Johnston et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0207889 A1 | 8/2013 | Chang et al. |
| 2013/0207963 A1 | 8/2013 | Stirbu et al. |
| 2013/0215235 A1 | 8/2013 | Russell |
| 2013/0217998 A1 | 8/2013 | Mahfouz et al. |
| 2013/0221996 A1 | 8/2013 | Poupyrev et al. |
| 2013/0222384 A1 | 8/2013 | Futterer |
| 2013/0232095 A1 | 9/2013 | Tan et al. |
| 2013/0259238 A1 | 10/2013 | Xiang et al. |
| 2013/0265229 A1 | 10/2013 | Forutanpour et al. |
| 2013/0265437 A1 | 10/2013 | Thorn et al. |
| 2013/0271292 A1 | 10/2013 | McDermott |
| 2013/0285901 A1 | 10/2013 | Lee et al. |
| 2013/0285913 A1 | 10/2013 | Griffin et al. |
| 2013/0293580 A1 | 11/2013 | Spivack |
| 2013/0310979 A1 | 11/2013 | Herr et al. |
| 2013/0312256 A1 | 11/2013 | Wesselmann et al. |
| 2013/0317382 A1 | 11/2013 | Le |
| 2013/0317648 A1* | 11/2013 | Assad ..................... A61B 5/389 700/258 |
| 2013/0332196 A1 | 12/2013 | Pinsker |
| 2013/0335302 A1 | 12/2013 | Crane et al. |
| 2014/0005743 A1 | 1/2014 | Giuffrida et al. |
| 2014/0020945 A1 | 1/2014 | Hurwitz et al. |
| 2014/0028539 A1 | 1/2014 | Newham et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0051946 A1 | 2/2014 | Arne et al. |
| 2014/0052150 A1 | 2/2014 | Taylor et al. |
| 2014/0074179 A1 | 3/2014 | Heldman et al. |
| 2014/0092009 A1 | 4/2014 | Yen et al. |
| 2014/0094675 A1 | 4/2014 | Luna et al. |
| 2014/0098018 A1 | 4/2014 | Kim et al. |
| 2014/0100432 A1 | 4/2014 | Golda et al. |
| 2014/0107493 A1 | 4/2014 | Yuen et al. |
| 2014/0121471 A1 | 5/2014 | Walker |
| 2014/0122958 A1 | 5/2014 | Greenebrg et al. |
| 2014/0132512 A1 | 5/2014 | Gomez Sainz-Garcia |
| 2014/0139422 A1 | 5/2014 | Mistry et al. |
| 2014/0142937 A1 | 5/2014 | Powledge et al. |
| 2014/0143064 A1 | 5/2014 | Tran |
| 2014/0147820 A1 | 5/2014 | Snow et al. |
| 2014/0157168 A1 | 6/2014 | Albouyeh et al. |
| 2014/0194062 A1 | 7/2014 | Palin et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0198944 A1 | 7/2014 | Forutanpour et al. |
| 2014/0200432 A1* | 7/2014 | Banerji ................. G16H 20/30 607/54 |
| 2014/0201666 A1 | 7/2014 | Bedikian et al. |
| 2014/0202643 A1 | 7/2014 | Hikmet et al. |
| 2014/0204455 A1 | 7/2014 | Popovich et al. |
| 2014/0223462 A1 | 8/2014 | Aimone et al. |
| 2014/0226193 A1 | 8/2014 | Sun |
| 2014/0232651 A1 | 8/2014 | Kress et al. |
| 2014/0236031 A1 | 8/2014 | Banet et al. |
| 2014/0240103 A1 | 8/2014 | Lake et al. |
| 2014/0240223 A1* | 8/2014 | Lake ....................... G06F 3/011 345/156 |
| 2014/0245200 A1 | 8/2014 | Holz |
| 2014/0249397 A1 | 9/2014 | Lake et al. |
| 2014/0257141 A1 | 9/2014 | Giuffrida et al. |
| 2014/0258864 A1 | 9/2014 | Shenoy et al. |
| 2014/0277622 A1 | 9/2014 | Raniere |
| 2014/0278139 A1 | 9/2014 | Hong et al. |
| 2014/0278441 A1 | 9/2014 | Ton et al. |
| 2014/0279860 A1 | 9/2014 | Pan et al. |
| 2014/0282282 A1 | 9/2014 | Holz |
| 2014/0285326 A1 | 9/2014 | Luna et al. |
| 2014/0285429 A1 | 9/2014 | Simmons |
| 2014/0297528 A1 | 10/2014 | Agrawal et al. |
| 2014/0299362 A1 | 10/2014 | Park et al. |
| 2014/0304665 A1 | 10/2014 | Holz |
| 2014/0310595 A1 | 10/2014 | Acharya et al. |
| 2014/0330404 A1 | 11/2014 | Abdelghani et al. |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1 | 11/2014 | Hisu et al. |
| 2014/0344731 A1 | 11/2014 | Holz |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0355825 A1 | 12/2014 | Kim et al. |
| 2014/0358024 A1 | 12/2014 | Nelson et al. |
| 2014/0358825 A1 | 12/2014 | Phillipps et al. |
| 2014/0359540 A1 | 12/2014 | Kelsey et al. |

(56) References Cited

U.S. PATENT DOCUMENTS

| | | |
|---|---|---|
| 2014/0361988 A1 | 12/2014 | Katz et al. |
| 2014/0364703 A1 | 12/2014 | Kim et al. |
| 2014/0365163 A1 | 12/2014 | Jallon |
| 2014/0368424 A1 | 12/2014 | Choi et al. |
| 2014/0368428 A1 | 12/2014 | Pinault |
| 2014/0368474 A1 | 12/2014 | Kim et al. |
| 2014/0368896 A1 | 12/2014 | Nakazono et al. |
| 2014/0375465 A1 | 12/2014 | Fenuccio et al. |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0011857 A1 | 1/2015 | Henson et al. |
| 2015/0019135 A1 | 1/2015 | Kacyvenski et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0036221 A1 | 2/2015 | Stephenson |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0065840 A1 | 3/2015 | Bailey |
| 2015/0070270 A1 | 3/2015 | Bailey et al. |
| 2015/0070274 A1 | 3/2015 | Morozov |
| 2015/0072326 A1 | 3/2015 | Mauri et al. |
| 2015/0084860 A1* | 3/2015 | Aleem .................. G06F 3/014 345/156 |
| 2015/0091790 A1 | 4/2015 | Forutanpour et al. |
| 2015/0094564 A1 | 4/2015 | Tashman et al. |
| 2015/0099946 A1 | 4/2015 | Sahin |
| 2015/0106052 A1 | 4/2015 | Balakrishnan et al. |
| 2015/0109202 A1* | 4/2015 | Ataee .................. A61B 5/681 345/156 |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0148728 A1 | 5/2015 | Sallum et al. |
| 2015/0157944 A1 | 6/2015 | Gottlieb |
| 2015/0160621 A1 | 6/2015 | Yilmaz |
| 2015/0169074 A1 | 6/2015 | Ataee et al. |
| 2015/0170421 A1 | 6/2015 | Mandella et al. |
| 2015/0177841 A1 | 6/2015 | Vanblon et al. |
| 2015/0182113 A1 | 7/2015 | Utter, II |
| 2015/0182130 A1 | 7/2015 | Utter, II |
| 2015/0182160 A1 | 7/2015 | Kim et al. |
| 2015/0182163 A1 | 7/2015 | Utter |
| 2015/0182164 A1 | 7/2015 | Utter, II |
| 2015/0182165 A1 | 7/2015 | Miller et al. |
| 2015/0185838 A1 | 7/2015 | Camacho-Perez et al. |
| 2015/0186609 A1 | 7/2015 | Utter, II |
| 2015/0187355 A1 | 7/2015 | Parkinson et al. |
| 2015/0193949 A1 | 7/2015 | Katz et al. |
| 2015/0199025 A1 | 7/2015 | Holz |
| 2015/0205126 A1 | 7/2015 | Schowengerdt |
| 2015/0205134 A1 | 7/2015 | Bailey et al. |
| 2015/0213191 A1 | 7/2015 | Abdelghani et al. |
| 2015/0216475 A1 | 8/2015 | Luna et al. |
| 2015/0220152 A1 | 8/2015 | Tait et al. |
| 2015/0223716 A1 | 8/2015 | Korkala et al. |
| 2015/0230756 A1 | 8/2015 | Luna et al. |
| 2015/0234426 A1 | 8/2015 | Bailey et al. |
| 2015/0237716 A1 | 8/2015 | Su et al. |
| 2015/0242009 A1 | 8/2015 | Xiao et al. |
| 2015/0242120 A1 | 8/2015 | Rodriguez |
| 2015/0242575 A1 | 8/2015 | Abovitz et al. |
| 2015/0261306 A1 | 9/2015 | Lake |
| 2015/0261318 A1 | 9/2015 | Scavezze et al. |
| 2015/0272483 A1 | 10/2015 | Etemad et al. |
| 2015/0277575 A1 | 10/2015 | Ataee et al. |
| 2015/0288944 A1 | 10/2015 | Nistico et al. |
| 2015/0289995 A1 | 10/2015 | Wilkinson et al. |
| 2015/0296553 A1 | 10/2015 | DiFranco et al. |
| 2015/0302168 A1 | 10/2015 | De Sapio et al. |
| 2015/0305672 A1 | 10/2015 | Grey et al. |
| 2015/0309563 A1 | 10/2015 | Connor |
| 2015/0309582 A1 | 10/2015 | Gupta |
| 2015/0310766 A1 | 10/2015 | Alshehri et al. |
| 2015/0312175 A1 | 10/2015 | Langholz |
| 2015/0313496 A1 | 11/2015 | Connor |
| 2015/0323998 A1 | 11/2015 | Kudekar et al. |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0351690 A1 | 12/2015 | Toth et al. |
| 2015/0355716 A1 | 12/2015 | Balasubramanian et al. |
| 2015/0355718 A1* | 12/2015 | Slonneger ............ G06F 3/0346 600/300 |
| 2015/0362734 A1 | 12/2015 | Moser et al. |
| 2015/0366504 A1 | 12/2015 | Connor |
| 2015/0370326 A1 | 12/2015 | Chapeskie et al. |
| 2015/0370333 A1* | 12/2015 | Ataee ..................... G06F 1/163 345/156 |
| 2015/0378161 A1 | 12/2015 | Bailey et al. |
| 2015/0378162 A1 | 12/2015 | Bailey et al. |
| 2015/0378164 A1 | 12/2015 | Bailey et al. |
| 2015/0379770 A1 | 12/2015 | Haley, Jr. et al. |
| 2016/0011668 A1 | 1/2016 | Gilad-Bachrach et al. |
| 2016/0020500 A1 | 1/2016 | Matsuda |
| 2016/0026853 A1 | 1/2016 | Wexler et al. |
| 2016/0033771 A1 | 2/2016 | Tremblay et al. |
| 2016/0049073 A1 | 2/2016 | Lee |
| 2016/0050037 A1 | 2/2016 | Webb |
| 2016/0071319 A1 | 3/2016 | Fallon et al. |
| 2016/0092504 A1 | 3/2016 | Mitri et al. |
| 2016/0099010 A1 | 4/2016 | Sainath et al. |
| 2016/0107309 A1 | 4/2016 | Walsh et al. |
| 2016/0113587 A1 | 4/2016 | Kothe et al. |
| 2016/0144172 A1 | 5/2016 | Hsueh et al. |
| 2016/0150636 A1 | 5/2016 | Otsubo |
| 2016/0156762 A1 | 6/2016 | Bailey et al. |
| 2016/0162604 A1 | 6/2016 | Xiaoli et al. |
| 2016/0170710 A1 | 6/2016 | Kim et al. |
| 2016/0187992 A1 | 6/2016 | Yamamoto et al. |
| 2016/0195928 A1 | 7/2016 | Wagner et al. |
| 2016/0199699 A1 | 7/2016 | Klassen |
| 2016/0202081 A1 | 7/2016 | Debieuvre et al. |
| 2016/0206206 A1 | 7/2016 | Avila et al. |
| 2016/0207201 A1 | 7/2016 | Herr et al. |
| 2016/0217614 A1 | 7/2016 | Kraver et al. |
| 2016/0235323 A1 | 8/2016 | Tadi et al. |
| 2016/0238845 A1 | 8/2016 | Alexander et al. |
| 2016/0239080 A1 | 8/2016 | Marcolina et al. |
| 2016/0242646 A1* | 8/2016 | Obma .................. A61B 5/1114 |
| 2016/0259407 A1 | 9/2016 | Schick |
| 2016/0262687 A1 | 9/2016 | Vaidyanathan et al. |
| 2016/0263458 A1 | 9/2016 | Mather et al. |
| 2016/0274365 A1 | 9/2016 | Bailey et al. |
| 2016/0274732 A1 | 9/2016 | Bang et al. |
| 2016/0274758 A1 | 9/2016 | Bailey |
| 2016/0275726 A1 | 9/2016 | Mullins |
| 2016/0282947 A1 | 9/2016 | Schwarz et al. |
| 2016/0291768 A1 | 10/2016 | Cho et al. |
| 2016/0292497 A1 | 10/2016 | Kehtarnavaz et al. |
| 2016/0309249 A1 | 10/2016 | Wu et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0314623 A1 | 10/2016 | Coleman et al. |
| 2016/0327796 A1 | 11/2016 | Bailey et al. |
| 2016/0327797 A1 | 11/2016 | Bailey et al. |
| 2016/0342227 A1 | 11/2016 | Natzke et al. |
| 2016/0349514 A1 | 12/2016 | Alexander et al. |
| 2016/0349515 A1 | 12/2016 | Alexander et al. |
| 2016/0349516 A1 | 12/2016 | Alexander et al. |
| 2016/0350973 A1 | 12/2016 | Shapira et al. |
| 2016/0377865 A1 | 12/2016 | Alexander et al. |
| 2016/0377866 A1 | 12/2016 | Alexander et al. |
| 2017/0025026 A1 | 1/2017 | Ortiz Catalan |
| 2017/0031502 A1 | 2/2017 | Rosenberg et al. |
| 2017/0035313 A1 | 2/2017 | Hong et al. |
| 2017/0061817 A1 | 3/2017 | Mettler May |

(56) References Cited

U.S. PATENT DOCUMENTS

| | | |
|---|---|---|
| 2017/0068095 A1 | 3/2017 | Holland et al. |
| 2017/0068445 A1 | 3/2017 | Lee et al. |
| 2017/0075426 A1 | 3/2017 | Camacho Perez et al. |
| 2017/0079828 A1 | 3/2017 | Pedtke et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0095178 A1 | 4/2017 | Schoen et al. |
| 2017/0097753 A1 | 4/2017 | Bailey et al. |
| 2017/0115483 A1 | 4/2017 | Aleem et al. |
| 2017/0119472 A1 | 5/2017 | Herrmann et al. |
| 2017/0123487 A1 | 5/2017 | Hazra et al. |
| 2017/0124474 A1 | 5/2017 | Kashyap |
| 2017/0124816 A1 | 5/2017 | Yang et al. |
| 2017/0127354 A1 | 5/2017 | Garland et al. |
| 2017/0147077 A1 | 5/2017 | Park et al. |
| 2017/0153701 A1 | 6/2017 | Mahon et al. |
| 2017/0161635 A1 | 6/2017 | Dono et al. |
| 2017/0188878 A1 | 7/2017 | Lee |
| 2017/0188980 A1 | 7/2017 | Ash |
| 2017/0197142 A1 | 7/2017 | Stafford et al. |
| 2017/0205876 A1 | 7/2017 | Vidal et al. |
| 2017/0209055 A1 | 7/2017 | Pantelopoulos et al. |
| 2017/0212290 A1 | 7/2017 | Alexander et al. |
| 2017/0212349 A1 | 7/2017 | Bailey et al. |
| 2017/0219829 A1 | 8/2017 | Bailey |
| 2017/0220923 A1 | 8/2017 | Bae et al. |
| 2017/0237789 A1 | 8/2017 | Harner et al. |
| 2017/0237901 A1 | 8/2017 | Lee et al. |
| 2017/0259167 A1 | 9/2017 | Cook et al. |
| 2017/0262064 A1 | 9/2017 | Ofir et al. |
| 2017/0277282 A1 | 9/2017 | Go |
| 2017/0285744 A1 | 10/2017 | Juliato |
| 2017/0285756 A1 | 10/2017 | Wang et al. |
| 2017/0285757 A1 | 10/2017 | Robertson et al. |
| 2017/0285848 A1 | 10/2017 | Rosenberg et al. |
| 2017/0296363 A1 | 10/2017 | Yetkin et al. |
| 2017/0299956 A1 | 10/2017 | Holland et al. |
| 2017/0301630 A1 | 10/2017 | Nguyen et al. |
| 2017/0308118 A1 | 10/2017 | Ito |
| 2017/0312614 A1 | 11/2017 | Tran et al. |
| 2017/0329392 A1 | 11/2017 | Keskin et al. |
| 2017/0329404 A1 | 11/2017 | Keskin et al. |
| 2017/0340506 A1 | 11/2017 | Zhang et al. |
| 2017/0344706 A1 | 11/2017 | Torres et al. |
| 2017/0347908 A1 | 12/2017 | Watanabe et al. |
| 2017/0371403 A1 | 12/2017 | Wetzler et al. |
| 2018/0000367 A1 | 1/2018 | Longinotti-Buitoni |
| 2018/0018825 A1 | 1/2018 | Kim et al. |
| 2018/0020285 A1 | 1/2018 | Zass |
| 2018/0020951 A1 | 1/2018 | Kaifosh et al. |
| 2018/0020978 A1 | 1/2018 | Kaifosh et al. |
| 2018/0020990 A1 | 1/2018 | Park et al. |
| 2018/0024634 A1 | 1/2018 | Kaifosh et al. |
| 2018/0024635 A1 | 1/2018 | Kaifosh et al. |
| 2018/0024641 A1 | 1/2018 | Mao et al. |
| 2018/0064363 A1 | 3/2018 | Morun et al. |
| 2018/0067553 A1 | 3/2018 | Morun et al. |
| 2018/0068489 A1 | 3/2018 | Kim et al. |
| 2018/0074332 A1 | 3/2018 | Li et al. |
| 2018/0081439 A1 | 3/2018 | Daniels |
| 2018/0088675 A1* | 3/2018 | Vogel ............... G06F 3/017 |
| 2018/0088765 A1 | 3/2018 | Bailey |
| 2018/0092599 A1 | 4/2018 | Kerth et al. |
| 2018/0093181 A1 | 4/2018 | Goslin et al. |
| 2018/0095542 A1 | 4/2018 | Mallinson |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0107275 A1 | 4/2018 | Chen et al. |
| 2018/0120948 A1 | 5/2018 | Aleem et al. |
| 2018/0133551 A1 | 5/2018 | Chang et al. |
| 2018/0140441 A1 | 5/2018 | Poirters |
| 2018/0150033 A1 | 5/2018 | Lake et al. |
| 2018/0153430 A1* | 6/2018 | Ang ............... A61B 5/4851 |
| 2018/0153444 A1 | 6/2018 | Yang et al. |
| 2018/0154140 A1 | 6/2018 | Bouton et al. |
| 2018/0168905 A1 | 6/2018 | Goodall et al. |
| 2018/0178008 A1 | 6/2018 | Bouton et al. |
| 2018/0217249 A1 | 8/2018 | La Salla et al. |
| 2018/0239430 A1 | 8/2018 | Tadi et al. |
| 2018/0240459 A1 | 8/2018 | Weng et al. |
| 2018/0247443 A1 | 8/2018 | Briggs et al. |
| 2018/0279919 A1 | 10/2018 | Bansbach et al. |
| 2018/0301057 A1 | 10/2018 | Hargrove et al. |
| 2018/0307314 A1 | 10/2018 | Connor |
| 2018/0314879 A1 | 11/2018 | Khwaja et al. |
| 2018/0321745 A1 | 11/2018 | Morun et al. |
| 2018/0321746 A1 | 11/2018 | Morun et al. |
| 2018/0330549 A1 | 11/2018 | Brenton |
| 2018/0333575 A1 | 11/2018 | Bouton |
| 2018/0344195 A1 | 12/2018 | Morun et al. |
| 2018/0356890 A1 | 12/2018 | Zhang et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0027141 A1 | 1/2019 | Strong et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0056422 A1 | 2/2019 | Park et al. |
| 2019/0076716 A1 | 3/2019 | Chiou et al. |
| 2019/0089898 A1 | 3/2019 | Kim et al. |
| 2019/0113973 A1 | 4/2019 | Coleman et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0196585 A1 | 6/2019 | Laszlo et al. |
| 2019/0196586 A1 | 6/2019 | Laszlo et al. |
| 2019/0197778 A1 | 6/2019 | Sachdeva et al. |
| 2019/0209034 A1* | 7/2019 | Deno ............... A61B 5/25 |
| 2019/0212817 A1 | 7/2019 | Kaifosh et al. |
| 2019/0216619 A1* | 7/2019 | McDonnall ............... A61B 5/296 |
| 2019/0223748 A1 | 7/2019 | Al-Natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0279407 A1 | 9/2019 | McHugh et al. |
| 2019/0294243 A1 | 9/2019 | Laszlo et al. |
| 2019/0324549 A1 | 10/2019 | Araki et al. |
| 2019/0332140 A1 | 10/2019 | Wang et al. |
| 2019/0348026 A1 | 11/2019 | Berenzweig et al. |
| 2019/0348027 A1 | 11/2019 | Berenzweig et al. |
| 2019/0357787 A1 | 11/2019 | Barachant et al. |
| 2019/0362557 A1 | 11/2019 | Lacey et al. |
| 2020/0042089 A1 | 2/2020 | Ang et al. |
| 2020/0057661 A1 | 2/2020 | Bendfeldt |
| 2020/0065569 A1 | 2/2020 | Nduka et al. |
| 2020/0069210 A1 | 3/2020 | Berenzweig et al. |
| 2020/0069211 A1 | 3/2020 | Berenzweig et al. |
| 2020/0073483 A1 | 3/2020 | Berenzweig et al. |
| 2020/0077955 A1* | 3/2020 | Shui ............... A61B 5/7203 |
| 2020/0097081 A1 | 3/2020 | Stone et al. |
| 2020/0097083 A1 | 3/2020 | Mao et al. |
| 2020/0111260 A1 | 4/2020 | Osborn et al. |
| 2020/0125171 A1 | 4/2020 | Morun et al. |
| 2020/0142490 A1 | 5/2020 | Xiong et al. |
| 2020/0143795 A1 | 5/2020 | Park et al. |
| 2020/0159322 A1 | 5/2020 | Morun et al. |
| 2020/0163562 A1 | 5/2020 | Neaves |
| 2020/0205932 A1* | 7/2020 | Zar ............... A61B 5/063 |
| 2020/0225320 A1 | 7/2020 | Belskikh et al. |
| 2020/0245873 A1 | 8/2020 | Frank et al. |
| 2020/0249752 A1 | 8/2020 | Parshionikar |
| 2020/0275895 A1 | 9/2020 | Barachant |
| 2020/0301509 A1 | 9/2020 | Liu et al. |
| 2020/0305795 A1* | 10/2020 | Floyd ............... A61B 5/6867 |
| 2020/0320335 A1 | 10/2020 | Shamun et al. |

(56) References Cited

U.S. PATENT DOCUMENTS

| | | | |
|---|---|---|---|
| 2021/0109598 A1 | 4/2021 | Zhang et al. | |
| 2021/0117523 A1 | 4/2021 | Kim et al. | |
| 2021/0290159 A1 | 9/2021 | Bruinsma et al. | |
| 2022/0256706 A1* | 8/2022 | Xiong | H05K 1/147 |

FOREIGN PATENT DOCUMENTS

| | | |
|---|---|---|
| CA | 2939644 A1 | 8/2015 |
| CN | 1838933 A | 9/2006 |
| CN | 102246125 A | 11/2011 |
| CN | 103777752 A | 5/2014 |
| CN | 105009031 A | 10/2015 |
| CN | 105190477 A | 12/2015 |
| CN | 105190578 A | 12/2015 |
| CN | 106102504 A | 11/2016 |
| CN | 110300542 A | 10/2019 |
| CN | 111902077 A | 11/2020 |
| CN | 112074225 A | 12/2020 |
| CN | 112469469 A | 3/2021 |
| CN | 112822992 A | 5/2021 |
| DE | 4412278 A1 | 10/1995 |
| EP | 0301790 A2 | 2/1989 |
| EP | 1345210 A2 | 9/2003 |
| EP | 1408443 B1 | 10/2006 |
| EP | 2198521 B1 | 6/2012 |
| EP | 2541763 A1 | 1/2013 |
| EP | 2733578 A2 | 5/2014 |
| EP | 2959394 A1 | 12/2015 |
| EP | 3104737 A1 | 12/2016 |
| EP | 3200051 A1 | 8/2017 |
| EP | 3487395 A1 | 5/2019 |
| EP | 2959394 B1 | 5/2021 |
| JP | S61198892 A | 9/1986 |
| JP | H05277080 A | 10/1993 |
| JP | H07248873 A | 9/1995 |
| JP | 3103427 B2 | 10/2000 |
| JP | 2002287869 A | 10/2002 |
| JP | 2003303047 A | 10/2003 |
| JP | 2005095561 A | 4/2005 |
| JP | 2005352739 A | 12/2005 |
| JP | 2008192004 A | 8/2008 |
| JP | 2009050679 A | 3/2009 |
| JP | 2010520561 A | 6/2010 |
| JP | 2013160905 A | 8/2013 |
| JP | 2016507851 A | 3/2016 |
| JP | 2017509386 A | 4/2017 |
| JP | 2019023941 A | 2/2019 |
| JP | 2021072136 A | 5/2021 |
| KR | 20110040165 A | 4/2011 |
| KR | 20120094870 A | 8/2012 |
| KR | 20120097997 A | 9/2012 |
| KR | 20150123254 A | 11/2015 |
| KR | 20160121552 A | 10/2016 |
| KR | 20170067873 A | 6/2017 |
| KR | 20170107283 A | 9/2017 |
| KR | 101790147 | 10/2017 |
| WO | 9527341 A1 | 10/1995 |
| WO | 2006086504 A2 | 8/2006 |
| WO | 2008109248 A2 | 9/2008 |
| WO | 2009042313 A1 | 4/2009 |
| WO | 2010104879 A2 | 9/2010 |
| WO | WO-2011011750 A1 | 1/2011 |
| WO | 2011070554 A2 | 6/2011 |
| WO | 2012155157 A1 | 11/2012 |
| WO | 2014130871 A1 | 8/2014 |
| WO | WO-2014155288 A2 | 10/2014 |
| WO | 2014186370 A1 | 11/2014 |
| WO | 2014194257 A1 | 12/2014 |
| WO | 2014197443 A1 | 12/2014 |
| WO | 2015027089 A1 | 2/2015 |
| WO | 2015073713 A1 | 5/2015 |
| WO | WO-2015063520 A1 | 5/2015 |
| WO | 2015081113 A1 | 6/2015 |
| WO | 2015100172 A1 | 7/2015 |
| WO | 2015123445 A1 | 8/2015 |
| WO | WO-2015123775 A1 | 8/2015 |
| WO | 2015184760 A1 | 12/2015 |
| WO | 2015192117 A1 | 12/2015 |
| WO | 2015199747 A1 | 12/2015 |
| WO | 2016041088 A1 | 3/2016 |
| WO | 2017062544 A1 | 4/2017 |
| WO | 2017075611 A1 | 5/2017 |
| WO | 2017092225 A1 | 6/2017 |
| WO | 2017120669 A1 | 7/2017 |
| WO | 2017172185 A1 | 10/2017 |
| WO | 2017208167 A1 | 12/2017 |
| WO | 2018022602 A1 | 2/2018 |
| WO | 2018098046 A2 | 5/2018 |
| WO | 2019099758 A1 | 5/2019 |
| WO | 2019147953 A1 | 8/2019 |
| WO | 2019147958 A1 | 8/2019 |
| WO | 2019147996 A1 | 8/2019 |
| WO | 2019217419 A2 | 11/2019 |
| WO | 2019226259 A1 | 11/2019 |
| WO | 2019231911 A1 | 12/2019 |
| WO | 2020047429 A1 | 3/2020 |
| WO | 2020061440 A1 | 3/2020 |
| WO | 2020061451 A1 | 3/2020 |
| WO | 2020072915 A1 | 4/2020 |

OTHER PUBLICATIONS

International Search Report and Written Opinion for International Application No. PCT/US2019/063587, dated Mar. 25, 2020, 16 pages.
International Preliminary Report on Patentability for International Application No. PCT/US2019/015238, dated Aug. 6, 2020, 7 pages.
International Preliminary Report on Patentability for International Application No. PCT/US2019/028299, dated Dec. 10, 2020, 11 pages.
International Preliminary Report on Patentability for International Application No. PCT/US2019/034173, dated Dec. 10, 2020, 9 pages.
International Preliminary Report on Patentability for International Application No. PCT/US2019/046351, dated Feb. 25, 2021, 8 pages.
International Preliminary Report on Patentability for International Application No. PCT/US2019/052131, dated Apr. 1, 2021, 8 pages.
International Preliminary Report on Patentability for International Application No. PCT/US2019/054716, dated Apr. 15, 2021, 10 pages.
International Preliminary Report on Patentability for International Application No. PCT/US2019/061759, dated May 27, 2021, 12 pages.
International Preliminary Report on Patentability for International Application No. PCT/US2020/049274, dated Mar. 17, 2022, 14 pages.
International Search Report and Written Opinion for International Application No. PCT/US2014/052143, dated Nov. 21, 2014, 8 Pages.
International Search Report and Written Opinion for International Application No. PCT/US2014/067443, dated Feb. 27, 2015, 8 pages.
International Search Report and Written Opinion for International Application No. PCT/US2015/015675, dated May 27, 2015, 9 Pages.
International Search Report and Written Opinion for International Application No. PCT/US2017/043686, dated Oct. 6, 2017, 9 Pages.
International Search Report and Written Opinion for International Application No. PCT/US2017/043693, dated Oct. 6, 2017, 7 Pages.
International Search Report and Written Opinion for International Application No. PCT/US2017/043791, dated Oct. 5, 2017, 10 Pages.
International Search Report and Written Opinion for International Application No. PCT/US2018/056768, dated Jan. 15, 2019, 8 pages.
International Search Report and Written Opinion for International Application No. PCT/US2018/061409, dated Mar. 12, 2019, 11 pages.

(56) References Cited

OTHER PUBLICATIONS

International Search Report and Written Opinion for International Application No. PCT/US2018/063215, dated Mar. 21, 2019, 17 Pages.
International Search Report and Written Opinion for International Application No. PCT/US2019/015167, dated May 21, 2019, 7 Pages.
International Search Report and Written Opinion for International Application No. PCT/US2019/015174, dated May 21, 2019, 8 pages.
International Search Report and Written Opinion for International Application No. PCT/US2019/015244, dated May 16, 2019, 8 Pages.
International Search Report and Written Opinion for International Application No. PCT/US2019/020065, dated May 16, 2019, 10 Pages.
International Search Report and Written Opinion for International Application No. PCT/US2019/028299, dated Aug. 9, 2019, 12 pages.
International Search Report and Written Opinion for International Application No. PCT/US2019/031114, dated Dec. 20, 2019, 18 Pages.
International Search Report and Written Opinion for International Application No. PCT/US2019/034173, dated Sep. 18, 2019, 10 Pages.
International Search Report and Written Opinion for International Application No. PCT/US2019/037302, dated Oct. 11, 2019, 13 Pages.
International Search Report and Written Opinion for International Application No. PCT/US2019/042579, dated Oct. 31, 2019, 8 Pages.
International Search Report and Written Opinion for International Application No. PCT/US2019/046351, dated Nov. 7, 2019, 9 pages.
International Search Report and Written Opinion for International Application No. PCT/US2019/049094, dated Jan. 9, 2020, 27 Pages.
International Search Report and Written Opinion for International Application No. PCT/US2019/052131, dated Dec. 6, 2019, 8 pages.
International Search Report and Written Opinion for International Application No. PCT/US2019/052151, dated Jan. 15, 2020, 10 pages.
International Search Report and Written Opinion for International Application No. PCT/US2019/054716, dated Dec. 20, 2019, 11 Pages.
International Search Report and Written Opinion for International Application No. PCT/US2019/061759, dated Jan. 29, 2020, 12 pages.
International Search Report and Written Opinion for International Application No. PCT/US2020/025735, dated Jun. 22, 2020, 10 pages.
International Search Report and Written Opinion for International Application No. PCT/US2020/025772, dated Aug. 3, 2020, 11 pages.
International Search Report and Written Opinion for International Application No. PCT/US2020/025797, dated Jul. 9, 2020, 10 pages.
International Search Report and Written Opinion for International Application No. PCT/US2020/049274, dated Feb. 1, 2021, 17 pages.
International Search Report and Written Opinion for International Application No. PCT/US2020/061392, dated Mar. 12, 2021, 12 pages.
International Search Report and Written Opinion for International Application No. PCT/US2017/043792, dated Oct. 5, 2017, 9 Pages.
International Search Report and Written Opinion for International Application No. PCT/US2019/015134, dated May 15, 2019, 11 Pages.
International Search Report and Written Opinion for International Application No. PCT/US2019/015180, dated May 28, 2019, 10 Pages.
International Search Report and Written Opinion for International Application No. PCT/US2019/015183, dated May 3, 2019, 8 Pages.
International Search Report and Written Opinion for International Application No. PCT/US2019/015238, dated May 16, 2019, 8 Pages.
Invitation to Pay Additional Fees for International Application No. PCT/US2019/031114, dated Aug. 6, 2019, 7 pages.
Invitation to Pay Additional Fees for International Application No. PCT/US2019/049094, dated Oct. 24, 2019, 2 Pages.
Jiang H., "Effective and Interactive Interpretation of Gestures by Individuals with Mobility Impairments," Thesis/Dissertation Acceptance, Purdue University Graduate School, Graduate School Form 30, Updated on Jan. 15, 2015, 24 pages.
Kainz et al., "Approach to Hand Tracking and Gesture Recognition Based on Depth-Sensing Cameras and EMG Monitoring," ACTA Informatica Pragensia, vol. 3, Jan. 1, 2014, pp. 104-112, Retrieved from the Internet: URL: https://aip.vse.cz/pdfs/aip/2014/01/08.pdf.
Kawaguchi J., et al., "Estimation of Finger Joint Angles Based on Electromechanical Sensing of Wrist Shape," IEEE Transactions on Neural Systems and Rehabilitation Engineering, Sep. 2017, vol. 25 (9), pp. 1409-1418.
Kim H., et al., "Real-Time Human Pose Estimation and Gesture Recognition from Depth Images Using Superpixels and SVM Classifier," Sensors, 2015, vol. 15, pp. 12410-12427.
Kipke D.R., et al., "Silicon-Substrate Intracortical Microelectrode Arrays for Long-Term Recording of Neuronal Spike Activity in Cerebral Cortex," IEEE Transactions on Neural Systems and Rehabilitation Engineering, Jun. 2003, vol. 11(2), 5 pages, Retrieved on Oct. 7, 2019 [Jul. 10, 2019] Retrieved from the Internet: URL: https://www.ece.uvic.ca/-pctill/papers/neurimp/Kipke_etal_2003_01214707.pdf.
Koerner M.D., "Design and Characterization of the Exo-Skin Haptic Device: A Novel Tendon Actuated Textile Hand Exoskeleton," Abstract of thesis for Drexel University Masters Degree [online], Nov. 2, 2017, 5 pages, Retrieved from the Internet: URL: https://dialog.proquest.com/professional/docview/1931047627?accountid=153692.
Al-Jumaily A., et al., "Electromyogram(EMG) Driven System based Virtual Reality for Prosthetic and Rehabilitation Devices," Proceedings of the 11th Internationalconference on Information Integration Andweb-Based Applications & Services, Jan. 1, 2009, pp. 582-586.
Al-Mashhadany Y.I., "Inverse Kinematics Problem (IKP) of 6-DOF Manipulator By Locally Recurrent Neural Networks (LRNNs)," Management and Service Science (MASS), International Conference on Management and Service Science., IEEE, Aug. 24, 2010, 5 pages.
Al-Timemy A.H., et al., "Improving the Performance Against Force Variation of EMG Controlled Multifunctional Upper-Limb Prostheses for Transradial Amputees," IEEE Transactions on Neural Systems and Rehabilitation Engineering, Jun. 2016, vol. 24 (6), 12 Pages.
Arkenbout E.A., et al., "Robust Hand Motion Tracking through Data Fusion of 5DT Data Glove and Nimble VR Kinect Camera Measurements," Sensors, 2015, vol. 15, pp. 31644-31671.
Benko H., et al., "Enhancing Input On and Above the Interactive Surface with Muscle Sensing," The ACM International Conference on Interactive Tabletops and Surfaces (ITS), Nov. 23-25, 2009, pp. 93-100.
Berenzweig A., et al., "Wearable Devices and Methods for Improved Speech Recognition," U.S. Appl. No. 16/785,680, filed Feb. 10, 2020, 67 pages.
Boyali A., et al., "Spectral Collaborative Representation based Classification for Hand Gestures Recognition on Electromyography Signals," Biomedical Signal Processing and Control, 2016, vol. 24, pp. 11-18.
Brownlee J., "Finite State Machines (FSM): Finite State Machines as a Control Technique in Artificial Intelligence (AI)," FSM, Jun. 2002, 12 pages.
Cannan J., et al., "A Wearable Sensor Fusion Armband for Simple Motion Control and Selection for Disabled and Non-Disabled Users," Computer Science and Electronic Engineering Conference, IEEE, Sep. 12, 2012, pp. 216-219, XP032276745.

(56) References Cited

OTHER PUBLICATIONS

Cheng J., et al., "A Novel Phonology- and Radical-Coded Chinese Sign Language Recognition Framework Using Accelerometer and Surface Electromyography Sensors," Sensors, 2015, vol. 15, pp. 23303-23324.
Communication Pursuant to Article 94(3) for European Patent Application No. 17835112.8, dated Dec. 14, 2020, 6 Pages.
Communication Pursuant to Rule 164(1) EPC, Partial Supplementary European Search Report for European Application No. 14753949.8, dated Sep. 30, 2016, 7 pages.
Co-pending U.S. Appl. No. 15/659,072, inventors Patrick; Kaifosh et al., filed Jul. 25, 2017.
Co-pending U.S. Appl. No. 15/816,435, inventors Ning; Guo et al., filed Nov. 17, 2017.
Co-pending U.S. Appl. No. 15/882,858, inventors Stephen; Lake et al., filed Jan. 29, 2018.
Co-pending U.S. Appl. No. 15/974,430, inventors Adam; Berenzweig et al., filed May 8, 2018.
Co-pending U.S. Appl. No. 16/353,998, inventors Patrick; Kaifosh et al., filed Mar. 14, 2019.
Co-pending U.S. Appl. No. 16/557,383, inventors Adam; Berenzweig et al., filed Aug. 30, 2019.
Co-pending U.S. Appl. No. 16/557,427, inventors Adam; Berenzweig et al., filed Aug. 30, 2019.
Co-Pending U.S. Appl. No. 15/974,430, filed May 8, 2018, 44 Pages.
Co-Pending U.S. Appl. No. 16/353,998, filed Mar. 14, 2019, 43 pages.
Co-Pending U.S. Appl. No. 16/557,383, filed Aug. 30, 2019, 94 Pages.
Co-Pending U.S. Appl. No. 16/557,427, filed Aug. 30, 2019, 93 Pages.
Co-Pending U.S. Appl. No. 16/577,207, filed Sep. 20, 2019, 67 Pages.
Co-Pending U.S. Appl. No. 14/505,836, filed Oct. 3, 2014, 59 Pages.
Co-Pending U.S. Appl. No. 15/816,435, filed Nov. 17, 2017, 24 Pages.
Co-Pending U.S. Appl. No. 15/882,858, filed Jan. 29, 2018, 54 Pages.
Co-Pending U.S. Appl. No. 15/974,384, filed May 8, 2018, 44 Pages.
Co-Pending U.S. Appl. No. 15/974,454, filed May 8, 2018, 45 Pages.
Co-Pending U.S. Appl. No. 16/557,342, filed Aug. 30, 2019, 93 Pages.
Corazza S., et al.,"A Markerless Motion Capture System to Study Musculoskeletal Biomechanics: Visual Hull and Simulated Annealing Approach," Annals of Biomedical Engineering, Jul. 2006, vol. 34 (6), pp. 1019-1029, [Retrieved on Dec. 11, 2019], 11 pages, Retrieved from the Internet: URL: https://www.researchgate.net/publication/6999610_A_Markerless_Motion_Capture_System_to_Study_Musculoskeletal_Biomechanics_Visual_Hull_and_Simulated_Annealing_Approach.
Costanza E., et al., "EMG as a Subtle Input Interface for Mobile Computing," Mobile HCI, LNCS 3160, 2004, pp. 426-430.
Costanza E., et al., "Toward Subtle Intimate Interfaces for Mobile Devices Using an EMG Controller," CHI, Proceedings of the SIGCHI Conference on Human Factors in Computing Systems, Apr. 2-7, 2005, pp. 481-489.
Cote-Allard U., et al., "Deep Learning for Electromyographic Hand Gesture Signal Classification Using Transfer Learning," IEEE Transactions on Neural Systems and Rehabilitation Engineering, Jan. 26, 2019, vol. 27 (4), 11 Pages.
Csapo A.B., et al., "Evaluation of Human-Myo Gesture Control Capabilities in Continuous Search and Select Operations," 7th IEEE International Conference on Cognitive Infocommunications, Oct. 16-18, 2016, pp. 000415-000420.

Davoodi R., et al., "Development of a Physics-Based Target Shooting Game to Train Amputee Users of Multi joint Upper Limb Prostheses," Presence, Massachusetts Institute of Technology, 2012, vol. 21 (1), pp. 85-95.
Delis A.L., et al., "Development of a Myoelectric Controller Based on Knee Angle Estimation," Biodevices, International Conference on Biomedical Electronics and Devices, Jan. 17, 2009, 7 pages.
Diener L., et al., "Direct Conversion From Facial Myoelectric Signals to Speech Using Deep Neural Networks," International Joint Conference on Neural Networks (IJCNN), Oct. 1, 2015, 7 pages.
Ding I-J., et al., "HMM with Improved Feature Extraction-Based Feature Parameters for Identity Recognition of Gesture Command Operators by Using a Sensed Kinect-Data Stream," Neurocomputing, 2017, vol. 262, pp. 108-119.
European Search Report for European Application No. 19861903.3, dated Oct. 12, 2021, 2 pages.
European Search Report for European Application No. 19863248.1, dated Oct. 19, 2021, 2 pages.
European Search Report for European Application No. 19868789.9, dated May 9, 2022, 9 pages.
Extended European Search Report for European Application No. 18879156.0, dated Mar. 12, 2021, 11 pages.
Extended European Search Report for European Application No. 19743717.1, dated Mar. 3, 2021, 12 pages.
Extended European Search Report for European Application No. 19744404.5, dated Mar. 29, 2021, 11 pages.
Extended European Search Report for European Application No. 19799947.7, dated May 26, 2021, 10 pages.
Extended European Search Report for European Application No. 17835111.0, dated Nov. 21, 2019, 6 pages.
Extended European Search Report for European Application No. 17835112.8, dated Feb. 5, 2020, 17 pages.
Extended European Search Report for European Application No. 17835140.9, dated Nov. 26, 2019, 10 Pages.
Extended European Search Report for European Application No. 18869441.8, dated Nov. 17, 2020, 20 Pages.
Lee D.C., et al., "Motion and Force Estimation System of Human Fingers," Journal of Institute of Control, Robotics and Systems, 2011, vol. 17 (10), pp. 1014-1020.
Li Y., et al., "Motor Function Evaluation of Hemiplegic Upper-Extremities Using Data Fusion from Wearable Inertial and Surface EMG Sensors," Sensors, MDPI, 2017, vol. 17 (582), pp. 1-17.
Lopes J., et al., "Hand/Arm Gesture Segmentation by Motion Using IMU and EMG Sensing," ScienceDirect, Jun. 27-30, 2017, vol. 11, pp. 107-113.
Marcard T.V., et al., "Sparse Inertial Poser: Automatic 3D Human Pose Estimation from Sparse IMUs," arxiv.org, Computer Graphics Forum, 2017, vol. 36 (2), 12 pages, XP080759137.
Martin H., et al., "A Novel Approach of Prosthetic Arm Control using Computer Vision, Biosignals, and Motion Capture," IEEE Symposium on Computational Intelligence in Robotic Rehabilitation and Assistive Technologies (CIR2AT), 2014, 5 pages.
McIntee S.S., "A Task Model of Free-Space Movement-Based Geastures," Dissertation, Graduate Faculty of North Carolina State University, Computer Science, 2016, 129 pages.
Mendes JR.J.J.A., et al., "Sensor Fusion and Smart Sensor in Sports and Biomedical Applications," Sensors, 2016, vol. 16 (1569), pp. 1-31.
Mohamed O.H., "Homogeneous Cognitive Based Biometrics for Static Authentication," Dissertation submitted to University of Victoria, Canada, 2010, [last accessed Oct. 11, 2019], 149 pages, Retrieved from the Internet: URL: http://hdl.handle.net/1828/321.
Morris D., et al., "Emerging Input Technologies for Always-Available Mobile Interaction," Foundations and Trends in Human-Computer Interaction, 2010, vol. 4 (4), pp. 245-316.
Naik G.R., et al., "Source Separation and Identification issues in Bio Signals: A Solution using Blind Source Separation," Chapter 4 of Recent Advances in Biomedical Engineering, Intech, 2009, 23 pages.
Naik G.R., et al., "Real-Time Hand Gesture Identification for Human Computer Interaction Based on ICA of Surface

(56) References Cited

OTHER PUBLICATIONS

Electromyogram," IADIS International Conference Interfaces and Human Computer Interaction, 2007, pp. 83-90.
Naik G.R., et al., "Subtle Hand Gesture Identification for HCI Using Temporal Decorrelation Source Separation BSS of Surface EMG," Digital Image Computing Techniques and Applications, IEEE Computer Society, 2007, pp. 30-37.
Negro F., et al., "Multi-Channel Intramuscular and Surface EMG Decomposition by Convolutive Blind Source Separation," Journal of Neural Engineering, Feb. 29, 2016, vol. 13, 18 Pages.
Non-Final Office Action dated Mar. 2, 2021 for U.S. Appl. No. 15/974,430, filed May 8, 2018, 32 Pages.
Non-Final Office Action dated Sep. 2, 2020 for U.S. Appl. No. 15/882,858, filed Jan. 29, 2018, 66 Pages.
Non-Final Office Action dated Aug. 3, 2020 for U.S. Application No. U.S. Appl. No. 16/593,446, filed Oct. 4, 2019, 44 pages.
Non-Final Office Action dated Jun. 3, 2021 for U.S. Appl. No. 15/816,435, filed Nov. 17, 2017, 32 Pages.
Non-Final Office Action dated Jun. 5, 2020 for U.S. Appl. No. 15/659,072, filed Jul. 25, 2017, 59 Pages.
Non-Final Office Action dated Sep. 6, 2019 for U.S. Application No. 16/424, 144, filed May 28, 2019, 11 Pages.
Non-Final Office Action dated Feb. 8, 2021 for U.S. Appl. No. 16/557,342, filed Aug. 30, 2019, 11 Pages.
Non-Final Office Action dated Oct. 8, 2020 for U.S. Appl. No. 16/577,207, filed Sep. 20, 2019, 51 Pages.
Non-Final Office Action dated Apr. 9, 2019 for U.S. Appl. No. 16/258,409, filed Jan. 25, 2019, 71 Pages.
Non-Final Office Action dated Aug. 11, 2021 for U.S. Appl. No. 16/577,207, filed Sep. 20, 2019, 35 Pages.
Non-Final Office Action dated Jun. 13, 2019 for U.S. Appl. No. 16/258,279, filed Jan. 25, 2019, 38 Pages.
Non-Final Office Action dated Jun. 15, 2020 for U.S. Appl. No. 16/557,342, filed Aug. 30, 2019, 46 Pages.
Non-Final Office Action dated Jan. 16, 2020 for U.S. Appl. No. 16/389,419, filed Apr. 19, 2019, 26 Pages.
Non-Final Office Action dated May 16, 2019 for U.S. Appl. No. 15/974,384, filed May 8, 2018, 13 Pages.
Non-Final Office Action dated May 16, 2019 for U.S. Appl. No. 15/974,430, filed May 8, 2018, 12 Pages.
Non-Final Office Action dated Nov. 19, 2019 for U.S. Appl. No. 16/577,207, filed Sep. 20, 2019, 32 Pages.
Non-Final Office Action dated Aug. 20, 2020 for U.S. Appl. No. 15/974,454, filed May 8, 2018, 59 Pages.
Non-Final Office Action dated Dec. 20, 2019 for U.S. Appl. No. 15/974,454, filed May 8, 2018, 41 Pages.
Non-Final Office Action dated Jan. 22, 2020 for U.S. Appl. No. 15/816,435, filed Nov. 17, 2017, 35 Pages.
Non-Final Office Action dated Oct. 22, 2019 for U.S. Appl. No. 16/557,342, filed Aug. 30, 2019, 16 Pages.
Non-Final Office Action dated Dec. 23, 2019 for U.S. Appl. No. 16/557,383, filed Aug. 30, 2019, 53 Pages.
Non-Final Office Action dated Dec. 23, 2019 for U.S. Appl. No. 16/557,427, filed Aug. 30, 2019, 52 Pages.
Non-Final Office Action dated Feb. 23, 2017 for U.S. Appl. No. 14/505,836, filed Oct. 3, 2014, 54 Pages.
Non-Final Office Action dated Jul. 23, 2020 for U.S. Application No. U.S. Appl. No. 16/593,446, filed Oct. 4, 2019, 28 pages.
Non-Final Office Action dated May 24, 2019 for U.S. Appl. No. 16/353,998, filed Mar. 14, 2019, 20 Pages.
Non-Final Office Action dated May 26, 2020 for U.S. Appl. No. 16/353,998, filed Mar. 14, 2019, 60 Pages.
Non-Final Office Action dated Nov. 27, 2020 for U.S. Appl. No. 16/258,279, filed Jan. 25, 2019, 44 Pages.
Non-Final Office Action dated Apr. 29, 2019 for U.S. Appl. No. 16/257,979, filed Jan. 25, 2019, 63 Pages.
Non-Final Office Action dated Apr. 30, 2019 for U.S. Appl. No. 15/659,072, filed Jul. 25, 2017, 99 Pages.
Non-Final Office Action dated Apr. 30, 2020 for U.S. Appl. No. 15/974,430, filed May 8, 2018, 57 Pages.

Non-Final Office Action dated Dec. 30, 2019 for U.S. Application No. U.S. Appl. No. 16/593,446, filed Oct. 4, 2019, 43 pages.
Non-Final Office Action dated Jun. 30, 2016 for U.S. Appl. No. 14/505,836, filed Oct. 3, 2014, 37 Pages.
Non-Final Office Action dated Oct. 30, 2019 for U.S. Appl. No. 15/882,858, filed Jan. 29, 2018, 22 Pages.
Notice of Allowance dated Nov. 2, 2020 for U.S. Appl. No. 15/974,454, filed May 8, 2018, 24 Pages.
Notice of Allowance dated Nov. 4, 2019 for U.S. Appl. No. 15/974,384, filed May 8, 2018, 39 Pages.
Notice of Allowance dated Feb. 6, 2020 for U.S. Appl. No. 16/424, 144, filed May 28, 2019, 28 Pages.
Notice of Allowance dated Feb. 9, 2022 for U.S. Appl. No. 15/882,858, filed Jan. 29, 2018, 9 pages.
Notice of Allowance dated May 18, 2022 for U.S. Appl. No. 15/882,858, filed Jan. 29, 2018, 10 pages.
Extended European Search Report for European Application No. 19806723.3, dated Jul. 7, 2021, 13 pages.
Extended European Search Report for European Application No. 19810524.9, dated Mar. 17, 2021, 11 pages.
Extended European Search Report for European Application No. 19850130.6, dated Sep. 1, 2021, 14 Pages.
Extended European Search Report for European Application No. 19855191.3, dated Dec. 6, 2021, 11 pages.
Extended European Search Report for European Application No. 19883839.3, dated Dec. 15, 2021, 7 pages.
Farina D., et al., "Man/Machine Interface Based on the Discharge Timings of Spinal Motor Neurons After Targeted Muscle Reinnervation," Nature Biomedical Engineering, Feb. 6, 2017, vol. 1, Article No. 0025, pp. 1-12.
Favorskaya M., et al., "Localization and Recognition of Dynamic Hand Gestures Based on Hierarchy of Manifold Classifiers," International Archives of the Photogrammetry, Remote Sensing and Spatial Information Sciences, May 25-27, 2015, vol. XL-5/W6, pp. 1-8.
Final Office Action dated Jun. 2, 2020 for U.S. Appl. No. 15/882,858, filed Jan. 29, 2018, 127 Pages.
Final Office Action dated Jun. 2, 2020 for U.S. Appl. No. 16/557,383, filed Aug. 30, 2019, 66 Pages.
Final Office Action dated Nov. 3, 2020 for U.S. Appl. No. 15/974,430, filed May 8, 2018, 27 Pages.
Final Office Action dated Feb. 4, 2020 for U.S. Appl. No. 16/577,207, filed Sep. 20, 2019, 76 Pages.
Final Office Action dated Feb. 4, 2021 for U.S. Appl. No. 15/882,858, filed Jan. 29, 2018, 42 Pages.
Final Office Action dated Jun. 5, 2020 for U.S. Appl. No. 16/557,427, filed Aug. 30, 2019, 95 Pages.
Final Office Action dated Oct. 8, 2020 for U.S. Appl. No. 16/557,342, filed Aug. 30, 2019, 73 Pages.
Final Office Action dated Apr. 9, 2020 for U.S. Appl. No. 15/974,454, filed May 8, 2018, 19 Pages.
Final Office Action dated Dec. 11, 2019 for U.S. Appl. No. 15/974,430, filed May 8, 2018, 30 Pages.
Final Office Action dated Jan. 13, 2021 for U.S. Appl. No. 16/577,207, filed Sep. 20, 2019, 91 Pages.
Final Office Action dated Dec. 18, 2019 for U.S. Appl. No. 16/258,279, filed Jan. 25, 2019, 45 Pages.
Final Office Action dated Feb. 19, 2021 for U.S. Appl. No. 16/258,279, filed Jan. 25, 2019, 58 Pages.
Final Office Action dated Sep. 23, 2020 for U.S. Appl. No. 15/816,435, filed Nov. 17, 2017, 70 Pages.
Final Office Action dated Jan. 28, 2020 for U.S. Appl. No. 16/557,342, filed Aug. 30, 2019, 15 Pages.
Final Office Action dated Jul. 28, 2017 for U.S. Appl. No. 14/505,836, filed Oct. 3, 2014, 52 Pages.
Final Office Action dated Jun. 28, 2021 for U.S. Appl. No. 16/557,342, filed Aug. 30, 2019, 11 Pages.
Final Office Action dated Nov. 29, 2019 for U.S. Appl. No. 15/659,072, filed Jul. 25, 2017, 36 Pages.
Final Office Action dated Nov. 29, 2019 for U.S. Appl. No. 16/353,998, filed Mar. 14, 2019, 33 Pages.

(56) References Cited

OTHER PUBLICATIONS

Fong H.C., et al., "PepperGram With Interactive Control," 22nd International Conference Onvirtual System & Multimedia (VSMM), Oct. 17, 2016, 5 pages.
International Preliminary Report on Patentability for International Application No. PCT/US2019/049094, dated Mar. 11, 2021, 24 Pages.
International Preliminary Report on Patentability for International Application No. PCT/US2019/052151, dated Apr. 1, 2021, 9 pages.
International Preliminary Report on Patentability for International Application No. PCT/US2014/017799, dated Sep. 3, 2015, 8 Pages.
International Preliminary Report on Patentability for International Application No. PCT/US2014/037863, dated Nov. 26, 2015, 8 pages.
International Preliminary Report on Patentability for International Application No. PCT/US2014/052143, dated Mar. 3, 2016, 7 pages.
International Preliminary Report on Patentability for International Application No. PCT/US2014/067443, dated Jun. 9, 2016, 7 pages.
International Preliminary Report on Patentability for International Application No. PCT/US2015/015675, dated Aug. 25, 2016, 8 Pages.
International Preliminary Report on Patentability for International Application No. PCT/US2017/043686, dated Feb. 7, 2019, 8 pages.
International Preliminary Report on Patentability for International Application No. PCT/US2017/043792, dated Feb. 7, 2019, 8 Pages.
International Preliminary Report on Patentability for International Application No. PCT/US2018/056768, dated Apr. 30, 2020, 7 pages.
International Preliminary Report on Patentability for International Application No. PCT/US2018/061409, dated May 28, 2020, 10 pages.
International Preliminary Report on Patentability for International Application No. PCT/US2019/015174, dated Aug. 6, 2020, 7 pages.
International Preliminary Report on Patentability for International Application No. PCT/US2019/015183, dated Aug. 6, 2020, 7 pages.
Notice of Allowance dated Nov. 10, 2021 for U.S. Appl. No. 15/882,858, filed Jan. 29, 2018, 6 pages.
Notice of Allowance dated Jul. 15, 2021 for U.S. Appl. No. 15/882,858, filed Jan. 29, 2018, 2 pages.
Notice of Allowance dated Dec. 16, 2020 for U.S. ApplicationNo. U.S. Appl. No. 16/593,446, filed Oct. 4, 2019, 44 pages.
Notice of Allowance dated May 18, 2020 for U.S. Appl. No. 16/258,279, filed Jan. 25, 2019, 42 Pages.
Notice of Allowance dated Aug. 19, 2020 for U.S. Appl. No. 16/557,427, filed Aug. 30, 2019, 22 Pages.
Notice of Allowance dated Jul. 19, 2019 for U.S. Appl. No. 16/258,409, filed Jan. 25, 2019, 36 Pages.
Notice of Allowance dated May 20, 2020 for U.S. Appl. No. 16/389,419, filed Apr. 19, 2019, 28 Pages.
Notice of Allowance dated Oct. 22, 2021 for U.S. Appl. No. 15/882,858, filed Jan. 29, 2018 , 8 pages.
Notice of Allowance dated Aug. 23, 2021 for U.S. Appl. No. 15/974,430, filed May 8, 2018, 12 pages.
Notice of Allowance dated Dec. 23, 2020 for U.S. Appl. No. 15/659,072, filed Jul. 25, 2017, 26 Pages.
Notice of Allowance dated Jun. 28, 2021 for U.S. Appl. No. 15/882,858, filed Jan. 29, 2018, 18 pages.
Notice of Allowance dated Jul. 31, 2019 for U.S. Appl. No. 16/257,979, filed Jan. 25, 2019, 22 Pages.
Office action for European Application No. 17835112.8, dated Feb. 11, 2022, 11 Pages.
Office Action for European Patent Application No. 19743717.1, dated Apr. 11, 2022, 10 pages.
Partial Supplementary European Search Report for European Application No. 18879156.0, dated Dec. 7, 2020, 9 pages.
Picard R.W., et al., "Affective Wearables," Proceedings of the IEEE 1st International Symposium on Wearable Computers, ISWC, Cambridge, MA, USA, Oct. 13-14, 1997, pp. 90-97.
Preinterview First Office Action dated Jun. 24, 2020 for U.S. Appl. No. 16/785,680, filed Feb. 10, 2020, 90 Pages.

Rekimoto J., "GestureWrist and GesturePad: Unobtrusive Wearable Interaction Devices," ISWC Proceedings of the 6th IEEE International Symposium on Wearable Computers, 2001, 7 pages.
Saponas T.S., et al., "Demonstrating the Feasibility of Using Forearm Electromyography for Muscle-Computer Interfaces," CHI Proceedings, Physiological Sensing for Input, Apr. 5-10, 2008, pp. 515-524.
Saponas T.S., et al., "Enabling Always-Available Input with Muscle-Computer Interfaces," Conference: Proceedings of the 22nd Annual ACM Symposium on User Interface Software and Technology, Oct. 7, 2009, pp. 167-176.
Saponas T.S., et al., "Making Muscle-Computer Interfaces More Practical," CHI, Atlanta, Georgia, USA, Apr. 10-15, 2010, 4 pages.
Sartori M., et al., "Neural Data-Driven Musculoskeletal Modeling for Personalized Neurorehabilitation Technologies," IEEE Transactions on Biomedical Engineering, May 5, 2016, vol. 63 (5), pp. 879-893.
Sato M., et al., "Touche: Enhancing Touch Interaction on Humans, Screens, Liquids, and Everyday Objects," CHI, Austin, Texas, May 5-10, 2012, 10 pages.
Sauras-Perez P., et al., "A Voice and Pointing Gesture Interaction System for Supporting Human Spontaneous Decisions in Autonomous Cars," Clemson University, All Dissertations, May 2017, 174 pages.
Shen S., et al., "I Am a Smartwatch and I Can Track My User's Arm," University of Illinois at Urbana-Champaign, MobiSys, Jun. 25-30, 2016, 12 pages.
Son M., et al., "EValuating the Utility of Two Gestural Discomfort Evaluation Methods," PLOS One, Apr. 19, 2017, 21 pages.
Strbac M., et al., "Microsoft Kinect-Based Artificial Perception System for Control of Functional Electrical Stimulation Assisted Grasping," Hindawi Publishing Corporation, BioMed Research International [online], 2014, Article No. 740469, 13 pages, Retrieved from the Internet: URL: https://dx.doi.org/10.1155/2014/740469.
Torres T., "Myo Gesture Control Armband," PCMag, Jun. 8, 2015, 9 pages, Retrieved from the Internet: URL: https://www.pcmag.com/article2/0,2817,2485462,00.asp.
Ueno A., et al., "A Capacitive Sensor System for Measuring Laplacian Electromyogram through Cloth: A Pilot Study," Proceedings of the 29th Annual International Conference of the IEEE EMBS, Cite Internationale, Lyon, France, Aug. 23-26, 2007, pp. 5731-5734.
Ueno A., et al., "Feasibility of Capacitive Sensing of Surface Electromyographic Potential through Cloth," Sensors and Materials, 2012, vol. 24 (6), pp. 335-346.
Valero-Cuevas F.J., et al., "Computational Models for Neuromuscular Function," IEEE Reviews in Biomedical Engineering, 2009, vol. 2, NIH Public Access Author Manuscript [online], Jun. 16, 2011 [Retrieved on Jul. 29, 2019], 52 pages, Retrieved from the Internet: URL: https://www.ncbi.nlm.nih.gov/pmc/articles/PMC3116649/.
Wittevrongel B., et al., "Spatiotemporal Beamforming: A Transparent and Unified Decoding Approach to Synchronous Visual Brain-Computer Interfacing," Frontiers in Neuroscience, Nov. 15, 2017, vol. 11, Article No. 630, 13 Pages.
Wodzinski M., et al., "Sequential Classification of Palm Gestures Based on A* Algorithm and MLP Neural Network for Quadrocopter Control," Metrology and Measurement Systems, 2017, vol. 24 (2), pp. 265-276.
Kiong A., et al., "A Novel HCI based on EMG and IMU," Proceedings of the 2011 IEEE International Conference on Robotics and Biomimetics, Phuket, Thailand, Dec. 7-11, 2011, pp. 2653-2657.
Xu Z., et al., "Hand Gesture Recognition and Virtual Game Control Based on 3D Accelerometer and EMG Sensors," Proceedings of the 14th International Conference on Intelligent User Interfaces, D211 Sanibel Island, Florida, Feb. 8-11, 2009, pp. 401-406.
Xue Y., et al., "Multiple Sensors Based Hand Motion Recognition Using Adaptive Directed Acyclic Graph," Applied Sciences, MDPI, 2017, vol. 7 (358), pp. 1-14.
Yang Z., et al., "Surface EMG Based Handgrip Force Predictions Using Gene Expression Programming," Neurocomputing, 2016, vol. 207, pp. 568-579.

(56) References Cited

OTHER PUBLICATIONS

Zacharaki E.I., et al., "Spike Pattern Recognition by Supervised Classification in Low Dimensional Embedding Space," Brain Informatics, 2016, vol. 3, pp. 73-83.
Zhang X., et al., "A Framework for Hand Gesture Recognition Based on Accelerometer and EMG Sensors," IEEE Transactions on Systems, Man, and Cybernetics—Part A: Systems and Humans, Nov. 2011, vol. 41 (6), pp. 1064-1076.
European Search Report for European Application No. 19890394.0, dated Apr. 29, 2022, 9 pages.
Tibold R., et al., "Prediction of Muscle Activity during Loaded Movements of The Upper Limb," Journal of NeuroEngineering Rehabilitation, 2015 vol. 12, No. 6, DOI: https://doi.org/10.1186/1743-0003-12-6, 12 pages.
Farina D., et al., "The Extraction of Neural Information from the Surface EMG for the Control of Upper-Limb Prostheses: Emerging Avenues and Challenges," IEEE Transactions on Neural Systems Andrehabilitation Engineering, vol. 22, No. 4, Jul. 1, 2014, pp. 797-809.
Office Action for European Application No. 19806723.3, dated Oct. 27, 2022, 8 pages.
Notice of Allowance dated Aug. 22, 2022 for U.S. Appl. No. 15/882,858, filed Jan. 29, 2018, 9 pages.
Amitai Y., "P-27: A Two-Dimensional Aperture Expander for Ultra-Compact, High-Performance Head-Worn Displays," SID Symposium Digest of Technical Papers, 2005, vol. 36 (1), pp. 360-363.
Ayras P., et al., "Exit Pupil Expander With a Large Field of View Based on Diffractive Optics," Journal of the SID, 2009, vol. 17 (8), pp. 659-664.
Bailey ct al., Wearable Muscle Interface Systems, Devices and Methods That Interact With Content Displayed on an Electronic Display, Office Action dated Mar. 31, 2015, for U.S. Appl. No. 14/155,107, 17 pages.
Bailey et al., "Muscle Interface Device and Method for Interacting With Content Displayed on Wearable Head Mounted Displays," Amendment filed Aug. 25, 2015, for U.S. Appl. No. 14/155,087, 10 pages.
Bailey et al., "Muscle Interface Device and Method for Interacting With Content Displayed on Wearable Head Mounted Displays," Amendment filed Aug. 9, 2016, for U.S. Appl. No. 14/155,087, 8 pages.
Bailey et al., "Muscle Interface Device and Method for Interacting With Content Displayed on Wearable Head Mounted Displays," Amendment filed May 17, 2016, for U.S. Appl. No. 14/155,087, 13 pages.
Bailey et al., "Muscle Interface Device and Method for Interacting With Content Displayed on Wearable Head Mounted Displays," Office Action dated Feb. 17, 2016, for U.S. Appl. No. 14/155,087, 16 pages.
Bailey et al., "Muscle Interface Device and Method for Interacting With Content Displayed on Wearable Head Mounted Displays," Office Action dated Jul. 20, 2015, for U.S. Appl. No. 14/155,087, 14 pages.
Bailey et al., "Muscle Interface Device and Method for Interacting With Content Displayed on Wearable Head Mounted Displays," Office Action dated Jul. 8, 2016, for U.S. Appl. No. 14/155,087, 16 pages.
Bailey et al., "Muscle Interface Device and Method for Interacting With Content Displayed on Wearable Head Mounted Displays," Office Action dated Mar. 31, 2015, for U.S. Appl. No. 14/155,087, 15 pages.
Bailey et al., "Muscle Interface Device and Method for Interacting With Content Displayed on Wearable Head Mounted Displays," Preliminary Amendment filed Jan. 28, 2014, for U.S. Appl. No. 14/155,087, 8 pages.
Bailey et al., "Wearable Muscle Interface Systems, Devices and Methods That Interact With. Content Displayed on an Electronic Display," Amendment filed Aug. 9, 2016, for U.S. Appl. No. 14/155,107, 8 pages.
Bailey et al., "Wearable Muscle Interface Systems, Devices and Methods That Interact With Content Displayed on an Electronic Display," Amendment filed May 11, 2016, for U.S. Appl. No. 14/155,107, 15 pages.
Bailey et al., Wearable Muscle Interface Systems, Devices and Methods That Interact With Content Displayed on an Electronic Display/ Office Action dated Feb. 11, 2016, for USAN U.S. Appl. No. 14/155,107, 20 pages.
Bailey et al., Wearable Muscle Interface Systems, Devices and Methods That Interact With Content Displayed on an Electronic Display, Office Action dated Jul. 16, 2015, for U.S. Appl. No. 14/155,107, 20 pages.
Bailey et al., Wearable Muscle Interface Systems. Devices and Methods That Interact With Content Displayed on an Electronic Display/ Office Action dated Jul. 8, 2016, for U.S. Appl. No. 14/155,107, 21 pages.
Bailey., et al., "Wearable Muscle Interface Systems, Devices and Methods That Interact With Content Displayed on an Electronic Display," Office Action dated Mar. 31, 2015, for U.S. Appl. No. 14/155,107, 17 pages.
Chellappan K.V., et al., "Laser-Based Displays: A Review," Applied Optics, Sep. 1, 2010, vol. 49 (25), pp. F79-F98.
Co-Pending U.S. Appl. No. 16/430,299, filed Jun. 3, 2019, 42 Pages.
Cui L., et al., "Diffraction From Angular Multiplexing Slanted Volume Hologram Gratings," Optik, 2005, vol. 116, pp. 118-122.
Curatu C., et al., "Dual Purpose Lens for an Eye-Tracked Projection Head-Mounted Display," International Optical Design Conference SPIE-OSA, 2006, vol. 6342, pp. 63420X-1-63420X-7.
Curatu C., et al., "Projection-Based Head-Mounted Display With Eye-Tracking Capabilities," Proceedings of SPIE, 2005, vol. 5875, pp. 58750J-1-58750J-9.
Essex D., "Tutorial on Optomechanical Beam Steering Mechanisms," OPTI 521 Tutorial, College of Optical Sciences, University of Arizona, 2006, 8 pages.
Fernandez E., et al., "Optimization of a Thick Polyvinyl Alcohol-Acrylamide Photopolymer for Data Storage Using a Combination of Angular and Peristrophic Holographic Multiplexing," Applied Optics, Oct. 10, 2009, vol. 45 (29), pp. 7661-7666.
Final Office Action dated Jan. 3, 2019 for U.S. Appl. No. 14/465,194, filed Aug. 21, 2014, 61 Pages.
Final Office Action dated Jan. 10, 2018 for U.S. Appl. No. 14/465,194, filed Aug. 21, 2014, 50 Pages.
Final Office Action dated Nov. 18, 2020 for U.S. Appl. No. 14/461,044, filed Aug. 15, 2014, 14 Pages.
Final Office Action dated Oct. 21, 2021 for U.S. Appl. No. 16/899,843, filed Jun. 12, 2020, 29 Pages.
Final Office Action dated Jul. 23, 2021 for U.S. Appl. No. 14/461,044, filed Aug. 15, 2014, 15 Pages.
Final Office Action received for U.S. Appl. No. 14/155,087 dated Dec. 16, 2016, 32 pages.
Final Office Action received for U.S. Appl. No. 14/155,087 dated Jul. 20, 2015, 27 pages.
Final Office Action received for U.S. Appl. No. 14/155,087 dated Jul. 8, 2016, 27 pages.
Final Office Action received for U.S. Appl. No. 14/155,087 dated Nov. 27, 2017, 40 pages.
Final Office Action received for U.S. Appl. No. 14/155,107 dated Dec. 19, 2016, 35 pages.
Final Office Action received for U.S. Appl. No. 14/155,107 dated Jan. 17, 2019, 46 pages.
Final Office Action received for U.S. Appl. No. 14/155,107 dated Jul. 16, 2015, 28 pages.
Final Office Action received for U.S. Appl. No. 14/155,107 dated Jul. 8, 2016, 31 pages.
Final Office Action received for U.S. Appl. No. 14/155,107 dated Nov. 27, 2017, 44 pages.
First Office Action mailed Nov. 25, 2020, for Canadian Application No. 2921954, filed Aug. 21, 2014, 4 pages.
Hainich R.R., et al., "Chapter 10: Near-Eye Displays," Displays: Fundamentals & Applications, AK Peters/CRC Press, 2011, 65 pages.
Hornstein S., et al., "Maradin's Micro-Mirror—System Level Synchronization Notes," SID Digest, 2012, pp. 981-984.

(56) References Cited

OTHER PUBLICATIONS

"IEEE 100 The Authoritative Dictionary of IEEE Standards Terms," Seventh Edition, Standards Information Network IEEE Press, Dec. 2000, 3 pages.
International Preliminary Report on Patentability for International Application No. PCT/US2020/061392, dated Jun. 9, 2022, 11 pages.
International Search Report and Written Opinion for International Application No. PCT/US2016/018293, dated Jun. 8, 2016, 17 Pages.
International Search Report and Written Opinion for International Application No. PCT/US2016/018298, dated Jun. 8, 2016, 14 Pages.
International Search Report and Written Opinion for International Application No. PCT/US2016/018299, dated Jun. 8, 2016, 12 Pages.
International Search Report and Written Opinion for International Application No. PCT/US2016/067246, dated Apr. 25, 2017, 10 Pages.
Itoh Y., et al., "Interaction-Free Calibration for Optical See-Through Head-Mounted Displays based on 3D Eye Localization," IEEE Symposium on 3D User Interfaces (3DUI), 2014, pp. 75-82.
Janssen C., "Radio Frequency (RF)," 2013, [Retrieved on Jul. 12, 2017], 2 pages, Retrieved from the Internet: URL: https://web.archive.org/web/20130726153946/https://www.techopedia.com/definition/5083/radio-frequency-rf.
Kessler D., "Optics of Near to Eye Displays (NEDs)," Presentation—Oasis, Tel Aviv, Feb. 19, 2013, 37 pages.
Krees B.C., et al., "Diffractive and Holographic Optics as Optical Combiners in Head Mounted Displays," UbiComp, Zurich, Switzerland, Sep. 8-12, 2013, pp. 1479-1482.
Kress B., et al., "A Review of Head-Mounted Displays (HMD) Technologies and Applications for Consumer Electronics," Proceedings of SPIE, 2013, vol. 8720, pp. 87200A-1-87200A-13.
Kress B., "Optical Architectures for See-Through Wearable Displays," Presentation, Bay Area SID Seminar, Apr. 30, 2014, 156 pages.
Lake et al., "Method and Apparatus for Analyzing Capacitive EMG and IMU Sensor Signals for Gesture Control," Amendment filed Aug. 21, 2015, for U.S. Appl. No. 14/186,878, 13 pages.
Lake et al., "Method and Apparatus for Analyzing Capacitive EMG and IMU Sensor Signals for Gesture Control," Office Action dated Jun. 17, 2015, for U.S. Appl. No. 14/186,878, 13 pages.
Lake et al. "Method and Apparatus for Analyzing Capacitive EMG and IMU Sensor Signals for Gesture Control," Preliminary Amendment filed May 9, 2014, for U.S. Appl. No. 14/186,878, 9 pages.
Lake et al., "Method and Apparatus for Analyzing Capacitive EMG and IMU Sensor Signals for Gesture Control," U.S. Appl. No. 14/186,878, filed Feb. 21, 2014, 29 pages.
Lake et al., "Methods and Devices for Combining Muscle Activity Sensor Signals and Inertial Sensor Signals for Gesture-Based Control," Amendment filed Jan. 8, 2016, for U.S. Appl. No. 14/186,889, 16 pages.
Lake et al., "Methods and Devices for Combining Muscle Activity Sensor Signals and Inertial Sensor Signals for Gesture-Based Control," Amendment filed Jul. 13, 2016, for U.S. Appl. No. 14/186,889, 12 pages.
Lake et al., "Methods and Devices for Combining Muscle Activity Sensor Signals and Inertial Sensor Signals for Gesture-Based Control," Office Action dated Jun. 16, 2016, for U.S. Appl. No. 14/186,889, 13 pages.
Lake et al., "Methods and Devices for Combining Muscle Activity Sensor Signals and Inertial Sensor Signals for Gesture-Based Control," Office Action dated Nov. 5, 2015, for U.S. Appl. No. 14/186,889, 11 pages.
Lake et al., "Methods and Devices That Combine Muscle Activity Sensor Signals and Inertial Sensor Signals for Gesture-Based Control," U.S. Appl. No. 14/186,889, filed Feb. 21, 2014, 58 pages.
Levola T., "7.1: Invited Paper: Novel Diffractive Optical Components for Near to Eye Displays," SID Symposium Digest of Technical Papers, 2006, vol. 37 (1), pp. 64-67.
Liao C.D., et al., "The Evolution of MEMS Displays," IEEE Transactions on Industrial Electronics, Apr. 2009, vol. 56 (4), pp. 1057-1065.
Lippert T.M., "Chapter 6: Display Devices: RSD™ (Retinal Scanning Display)," The Avionics Handbook, CRC Press, 2001, 8 pages.
Majaranta P., et al., "Chapter 3: Eye Tracking and Eye-Based Human-Computer Interaction," Advances in Physiological Computing, Springer-Verlag London, 2014, pp. 39-65.
Merriam-Webster, "Radio Frequencies," download date Jul. 12, 2017, 2 pages, Retrieved from the Internet: URL: https://www.merriam-webster.com/table/collegiate/radiofre.htm.
Morun C., et al., "Systems, Articles, and Methods for Capacitive Electromyography Sensors," U.S. Appl. No. 16/437,351, filed Jun. 11, 2019, 51 pages.
Non-Final Office Action dated Mar. 1, 2018 for U.S. Appl. No. 14/553,657, filed Nov. 25, 2014, 29 Pages.
Non-Final Office Action dated May 2, 2018 for U.S. Appl. No. 15/799,628, filed Oct. 31, 2017, 25 Pages.
Non-Final Office Action dated Oct. 5, 2022 for U.S. Appl. No. 17/576,815, filed Jan. 14, 2022, 14 pages.
Non-Final Office Action dated Nov. 6, 2018 for U.S. Appl. No. 16/057,573, filed Aug. 7, 2018, 14 Pages.
Non-Final Office Action dated May 7, 2021 for U.S. Appl. No. 16/899,843, filed Jun. 12, 2020, 24 Pages.
Non-Final Office Action dated Oct. 7, 2022 for U.S. Appl. No. 17/141,646, filed Jan. 5, 2021, 6 pages.
Non-Final Office Action dated Sep. 11, 2019 for U.S. Appl. No. 14/465,194, filed Aug. 21, 2014, 72 Pages.
Non-Final Office Action dated May 12, 2022 for U.S. Appl. No. 16/899,843, filed Jun. 12, 2020, 34 Pages.
Non-Final Office Action dated Sep. 14, 2017 for U.S. Appl. No. 14/539,773, filed Nov. 12, 2014, 28 pages.
Non-Final Office Action dated Aug. 15, 2018 for U.S. Appl. No. 14/465,194, filed Aug. 21, 2014, 64 Pages.
Non-Final Office Action dated Jun. 15, 2020 for U.S. Appl. No. 16/292,609, filed Mar. 5, 2019, 26 Pages.
Non-Final Office Action dated Aug. 17, 2017 for U.S. Appl. No. 14/465,194, filed Aug. 21, 2014, 81 Pages.
Non-Final Office Action dated Dec. 17, 2018 for U.S. Appl. No. 16/137,960, filed Sep. 21, 2018, 10 pages.
Non-Final Office Action dated Jan. 18, 2018 for U.S. Appl. No. 15/799,621, filed Oct. 31, 2017, 10 pages.
Non-Final Office Action dated Jun. 22, 2017 for U.S. Appl. No. 14/461,044, filed Aug. 15, 2014, 21 Pages.
Non-Final Office Action dated Feb. 25, 2021 for U.S. Appl. No. 14/461,044, filed Aug. 15, 2014, 17 Pages.
Non-Final Office Action dated Aug. 28, 2018 for U.S. Appl. No. 16/023,278, filed Jun. 29, 2018, 10 pages.
Non-Final Office Action dated Aug. 28, 2018 for U.S. Appl. No. 16/023,300, filed Jun. 29, 2018, 11 pages.
Non-Final Office Action dated Jun. 28, 2021 for U.S. Appl. No. 16/550,905, filed Aug. 26, 2019, 5 Pages.
Non-Final Office Action received for U.S. Appl. No. 14/155,087 dated Aug. 16, 2016, 28 pages.
Non-Final Office Action received for U.S. Appl. No. 14/155,087 dated Aug. 7, 2017, 28 pages.
Non-Final Office Action received for U.S. Appl. No. 14/155,087 dated Feb. 17, 2016, 26 pages.
Non-Final Office Action received for U.S. Appl. No. 14/155,087 dated Mar. 31, 2015, 22 pages.
Non-Final Office Action received for U.S. Appl. No. 14/155,107 dated Aug. 17, 2016, 37 pages.
Non-Final Office Action received for U.S. Appl. No. 14/155,107 dated Aug. 7, 2017, 34 pages.
Non-Final Office Action received for U.S. Appl. No. 14/155,107 dated Feb. 11, 2016, 42 pages.
Non-Final Office Action received for U.S. Appl. No. 14/155,107 dated Jul. 13, 2018, 45 pages.
Non-Final Office Action received for U.S. Appl. No. 14/155,107 dated Mar. 31, 2015, 26 pages.

(56) References Cited

OTHER PUBLICATIONS

Notice of Allowance dated May 1, 2019 for U.S. Appl. No. 16/137,960, filed Sep. 21, 2018, 14 pages.
Notice of Allowance dated Mar. 5, 2019 for U.S. Appl. No. 16/057,573, filed Aug. 7, 2018, 31 Pages.
Notice of Allowance dated Feb. 8, 2019 for U.S. Appl. No. 16/023,276, filed Jun. 29, 2018, 15 pages.
Notice of Allowance dated Mar. 11, 2020 for U.S. Application No. 14/465,194, filed Aug. 21, 2014, 29 Pages.
Notice of Allowance dated Jun. 15, 2018 for U.S. Appl. No. 15/799,621, filed Oct. 31, 2017, 27 pages.
Notice of Allowance dated Jul. 18, 2022 for U.S. Appl. No. 16/550,905, filed Aug. 26, 2019, 7 pages.
Notice of Allowance dated Apr. 20, 2022 for U.S. Appl. No. 14/461,044, filed Aug. 15, 2014, 08 pages.
Notice of Allowance dated Sep. 24, 2020 for U.S. Appl. No. 16/292,609, filed Mar. 5, 2019, 20 Pages.
Notice of Allowance dated Mar. 25, 2022 for U.S. Appl. No. 16/556,905, filed Aug. 26, 2019, 7 pages.
Notice of Allowance dated Sep. 25, 2018 for U.S. Appl. No. 14/553,657, filed Nov. 25, 2014, 25 pages.
Notice of Allowance dated Jan. 28, 2019 for U.S. Appl. No. 16/023,300, filed Jun. 29, 2018, 31 pages.
Notice of Allowance dated Nov. 3, 2022 for U.S. Appl. No. 16/899,843, filed Jun. 12, 2020, 10 pages.
Notice of Allowance dated Mar. 30, 2018 for U.S. Appl. No. 14/539,773, filed Nov. 12, 2014, 17 pages.
Notice of Allowance dated Nov. 30, 2018 for U.S. Appl. No. 15/799,628, filed Oct. 31, 2017, 19 Pages.
Notice of Allowance received for U.S. Appl. No. 14/155,107, dated Aug. 30, 2019, 16 pages.
Office Action dated Sep. 28, 2022 for Chinese Application No. 201780059093.7, filed Jul. 25, 2017, 16 pages.
Restriction Requirement dated Aug. 8, 2017 for U.S. Appl. No. 14/553,657, filed Nov. 25, 2014, 7 Pages.
Schowengerdt B.T., et al., "Stereoscopic Retinal Scanning Laser Display With Integrated Focus Cues for Ocular Accommodation," Proceedings of SPEE-IS&T Electronic Imaging, 2004, vol. 5291, pp. 355-376.
Silverman N.L., et al., "58.5L: Late-News Paper: Engineering a Retinal Scanning Laser Dispiay with Integrated Accommodative Depth Cues," SID 03 Digest, 2003, pp. 1538-1541.
Takatsuka Y., et al., "Retinal Projection Display Using Diffractive Optical Element," Tenth International Conference on Intelligent Information Hiding and Multimedia Signal Processing, IEEE, 2014, pp. 403-406.
Urey H., "Diffractive Exit-Pupil Expander for Display Applications," Applied Optics, Nov. 10, 2001, vol. 40 (32), pp. 5840-5851.
Urey H., et al., "Optical Performance Requirements for MEMS-Scanner Based Microdisplays," Conferences on MOEMS and Miniaturized Systems, SPIE, 2000, vol. 4178, pp. 176-185.

Viirre E., et al., "The Virtual Retinal Display: A New Technology for Virtual Reality and Augmented Vision in Medicine," Proceedings of Medicine Meets Virtual Reality, IOS Press and Ohmsha, 1998, pp. 252-257.
Wijk U., et al., "Forearm Amputee's Views of Prosthesis Use and Sensory Feedback," Journal of Hand Therapy, Jul. 2015, vol. 28 (3), pp. 269-278.
Written Opinion for International Application No. PCT/US2014/057029, dated Feb. 24, 2015, 9 Pages.
Notice of Allowance dated Dec. 14, 2022 for U.S. Appl. No. 15/882,858, filed Jan. 29, 2018, 10 pages.
Office Action dated Jan. 20, 2023 for Chinese Application No. 201780059093.7, filed Jul. 25, 2017, 16 pages.
Office Action dated Feb. 7, 2023 for European Application No. 19810524.9, filed May 28, 2019, 7 pages.
Gallina A., et al., "Surface EMG Biofeedback," Surface Electromyography: Physiology, Engineering, and Applications, 2016, pp. 485-500.
Gargiulo G., et al., "Giga Ohm High-Impedance FET Input Amplifiers for Dry Electrode Biosensor Circuits and Systems," Integrated Microsystems: Electronics, Photonics, and Biotechnolgy, Dec. 19, 2017, 41 Pages, Retrieved from the Internet: URL: https://www.researchgate.net/publication/255994293_Giga-Ohm_High-Impedance_FET_Input_Amplifiers_for_Dry_Electrode_Biosensor_Circuits_and_Systems.
Ghasemzadeh H., et al., "A Body Sensor Network With Electromyogram and Inertial Sensors: Multimodal Interpretation of Muscular Activities," IEEE Transactions on Information Technology in Biomedicine, Mar. 2010, vol. 14 (2), pp. 198-206.
Gopura R.A.R.C., et al., "A Human Forearm and Wrist Motion Assist Exoskeleton Robot With EMG-Based Fuzzy-Neuro Control," Proceedings of the 2nd Biennial IEEE/RAS-EMBS International Conference on Biomedical Robotics and Biomechatronics, Oct. 19-22, 2008, 6 pages.
Gourmelon L., et al., "Contactless Sensors for Surface Electromyography," Proceedings of the 28th IEEE EMBS Annual International Conference, New York City, NY, Aug. 30-Sep. 3, 2006, pp. 2514-2517.
Hauschild M., et al., "A Virtual Reality Environment for Designing and Fitting Neural Prosthetic Limbs," IEEE Transactions on Neural Systems and Rehabilitation Engineering, Mar. 2007, vol. 15 (1), pp. 9-15.
International Search Report and Written Opinion for International Application No. PCT/US2014/017799, dated May 16, 2014, 9 pages.
International Search Report and Written Opinion for International Application No. PCT/US2014/037863, dated Aug. 21, 2014, 10 pages.
International Preliminary Report on Patentability for International Application No. PCT/US2017/043693, dated Feb. 7, 2019, 7 Pages.
International Preliminary Report on Patentability for International Application No. PCT/US2017/043791, dated Feb. 7, 2019, 9 Pages.
International Preliminary Report on Patentability for International Application No. PCT/US2019/031114, dated Nov. 19, 2020, 16 pages.

\* cited by examiner

METHODS AND APPARATUS FOR AUTOCALIBRATION OF A WEARABLE ELECTRODE SENSOR SYSTEM

RELATED APPLICATIONS

This application claims priority under 35 U.S.C. § 119(e) to U.S. Provisional Application 62/771,957, filed Nov. 27, 2018, and entitled, "METHODS AND APPARATUS FOR AUTOCALIBRATION OF A WEARABLE SURFACE EMG SENSOR SYSTEM," the entire contents of which is incorporated by reference herein.

BACKGROUND

Some smart wearable devices that detect user-generated signals can be worn by users in various orientations and positions on the body. A common issue for these types of devices is that signal detection can be negatively affected if the wearable device is worn at a location or in an orientation for which the device was not optimized for performance.

SUMMARY

Some embodiments are directed to a system for calibrating the position and/or orientation of a wearable device configured to be worn on a wrist or forearm of a user. The system comprises a plurality of sensors arranged on the wearable device, wherein the plurality of sensors are configured to continuously sense a plurality of neuromuscular signals from the user, and at least one computer processor. The at least one computer processor is programmed to provide the plurality of neuromuscular signals and/or signals derived from the plurality of neuromuscular signals as inputs to one or more trained autocalibration models, determine based, at least in part, on the output of the one or more trained autocalibration models, a current position and/or orientation of the wearable device on the user, and generate a control signal based, at least in part, on the current position and/or orientation of the wearable device on the user and the plurality of neuromuscular signals.

In one aspect, the at least one computer processor is programmed to determine the current position and/or orientation of the wearable device on the user without the user performing a particular pose or gesture during sensing of the plurality of neuromuscular signals.

In another aspect, the at least one computer processor is programmed to process the sensed plurality of neuromuscular signals prior to providing the processed neuromuscular signals to the one or more autocalibration models.

In another aspect, the at least one programmed processor is further programmed to generate calibrated neuromuscular signals based, at least in part, on the current position and/or orientation of the wearable device and the plurality of neuromuscular signals, and generating a control signal comprises generating a control signal based, at least in part, on the calibrated neuromuscular signals.

In another aspect, the at least one programmed processor is further programmed to select or modify one or more inference models based, at least in part, on the current position and/or orientation of the wearable device, and provide the plurality of neuromuscular signals as input to the selected or modified one or more inference models, and generating a control signal is further based, at least in part, on an output of the selected or modified one or more inference models.

In another aspect, the one or more autocalibration models used to determine the current position and/or orientation of the wearable device on the user include a neural network.

In another aspect, the neural network is an LSTM neural network.

In another aspect, the LSTM neural network includes at least one pooling layer.

In another aspect, the at least one pooling layer comprises a max pooling layer.

In another aspect, the at least one pooling layer provides rotation invariance of ±1 sensor locations.

In another aspect, the one or more autocalibration models are trained to identify the orientation and/or location of the wearable device based on neuromuscular signals obtained from a plurality of users.

In another aspect, the neuromuscular signals obtained from a plurality of users were obtained as each of the plurality of users performed a plurality of hand gestures and/or poses while the wearable device was oriented and/or positioned in multiple different configurations on a forearm and/or wrist of the user.

In another aspect, the plurality of neuromuscular sensors comprises a plurality of electromyography (EMG) sensors.

In another aspect, the at least one computer processor is further programmed to identify that at least a portion of the wearable device has moved on the wrist or forearm of the user, and determine the current position and/or orientation of the wearable device on the user in response to identifying that at least a portion of the wearable device has moved on the wrist or forearm of the user.

In another aspect, identifying the at least a portion of the wearable device has moved on the wrist or forearm of the user comprises determining that the wearable device has rotated around and/or translated along the user's wrist or forearm.

In another aspect, identifying the at least a portion of the wearable device has moved on the wrist or forearm of the user comprises detecting one or more movement artifacts in the sensed plurality of neuromuscular signals.

In another aspect, the system further comprises at least one inertial measurement unit (IMU) sensor, and identifying the at least a portion of the wearable device has moved on the wrist or forearm of the user is based, at least in part, on at least one signal sensed by the at least one IMU sensor.

In another aspect, determining the current position and/or orientation of wearable device comprises determining a rotation of the wearable device relative to a virtual reference orientation of the wearable device.

In another aspect, the control signal is a control signal to control one or more operations of or within a virtual reality system or an augmented reality system.

Some embodiments are directed to a method for calibrating the position and/or orientation of a wearable band on a user. The method comprises sensing a plurality of neuromuscular signals from the user using a plurality of sensors arranged on the wearable device, providing the plurality of neuromuscular signals and/or signals derived from the plurality of neuromuscular signals as inputs to one or more trained autocalibration models, determining based, at least in part, on the output of the one or more trained autocalibration models, a current position and/or orientation of the wearable device on the user, and generating a control signal based, at least in part, on the current position and/or orientation of the wearable device on the user and the plurality of neuromuscular signals.

In one aspect, determining the current position and/or orientation of the wearable device comprises determining the current position and/or orientation of the wearable device without the user performing a particular pose or gesture during sensing of the plurality of neuromuscular signals.

In another aspect, the method further comprises processing the sensed plurality of neuromuscular signals prior to providing the processed neuromuscular signals to the one or more autocalibration models.

In another aspect, the method further comprises generating calibrated neuromuscular signals based, at least in part, on the current position and/or orientation of the wearable device and the plurality of neuromuscular signals, and generating a control signal comprises generating a control signal based, at least in part, on the calibrated neuromuscular signals.

In another aspect, the method further comprises selecting or modifying one or more inference models based, at least in part, on the current position and/or orientation of the wearable device, and providing the plurality of neuromuscular signals as input to the selected or modified one or more inference models, wherein generating a control signal is further based, at least in part, on an output of the selected or modified one or more inference models.

In another aspect, the one or more autocalibration models used to determine the current position and/or orientation of the wearable device on the user include a neural network.

In another aspect, the one or more autocalibration models are trained to identify the orientation and/or location of the wearable device based on neuromuscular signals obtained from a plurality of users.

In another aspect, the neuromuscular signals obtained from a plurality of users were obtained as each of the plurality of users performed a plurality of hand gestures and/or poses while the wearable device was oriented and/or positioned in multiple different configurations on a forearm and/or wrist of the user.

In another aspect, determining the current position and/or orientation of wearable device comprises determining a rotation of the wearable device relative to a virtual reference orientation of the wearable device.

In another aspect, the method further comprises identifying that at least a portion of the wearable device has moved on the wrist or forearm of the user, and determining the current position and/or orientation of the wearable device on the user in response to identifying that at least a portion of the wearable device has moved on the wrist or forearm of the user.

In another aspect, identifying the at least a portion of the wearable device has moved on the wrist or forearm of the user comprises determining that the wearable device has rotated around and/or translated along the user's wrist or forearm.\

In another aspect, identifying the at least a portion of the wearable device has moved on the wrist or forearm of the user comprises detecting one or more movement artifacts in the sensed plurality of neuromuscular signals.

In another aspect, the method further comprises identifying the at least a portion of the wearable device has moved on the wrist or forearm of the user is based, at least in part, on at least one signal sensed by at least one inertial measurement unit (IMU) sensor.

Some embodiments are directed to a method for training an inference model for autocalibration of a wearable device. The method comprises receiving neuromuscular signals sensed from a plurality of users as the wearable device was worn by each of the users while performing a plurality of hand gestures and/or poses, wherein for each of the plurality of hand gestures and/or poses, the wearable device was oriented or positioned differently on the user, labeling the received neuromuscular signals for each of the plurality of hand gestures and/or poses based on the orientation or position of the wearable device during sensing of the corresponding neuromuscular signals, and training one or more autocalibration models based, at least in part, on the labeled neuromuscular signals.

In one aspect, the method further comprises extracting from the received neuromuscular signals, a plurality of templates, where each of the plurality of templates corresponds to one of the plurality of hand gestures and/or poses, and generating calibrated neuromuscular signals based, at least on the extracted plurality of templates, and training the one or more autocalibration models comprises training the one or more autocalibration models based, at least in part, on the calibrated neuromuscular signals.

In another aspect, the method further comprises predicting a plurality of rotation offsets of the wearable device using a plurality of simulations of different orientations.

In another aspect, the one or more autocalibration models include a neural network.

In another aspect, the neural network is an LSTM neural network.

Some embodiments are directed to a non-transitory computer-readable storage medium encoded with a plurality of processor-executable instructions that, when executed by one or more computer processors perform one or more of the foregoing methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure arc contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Figure 1:
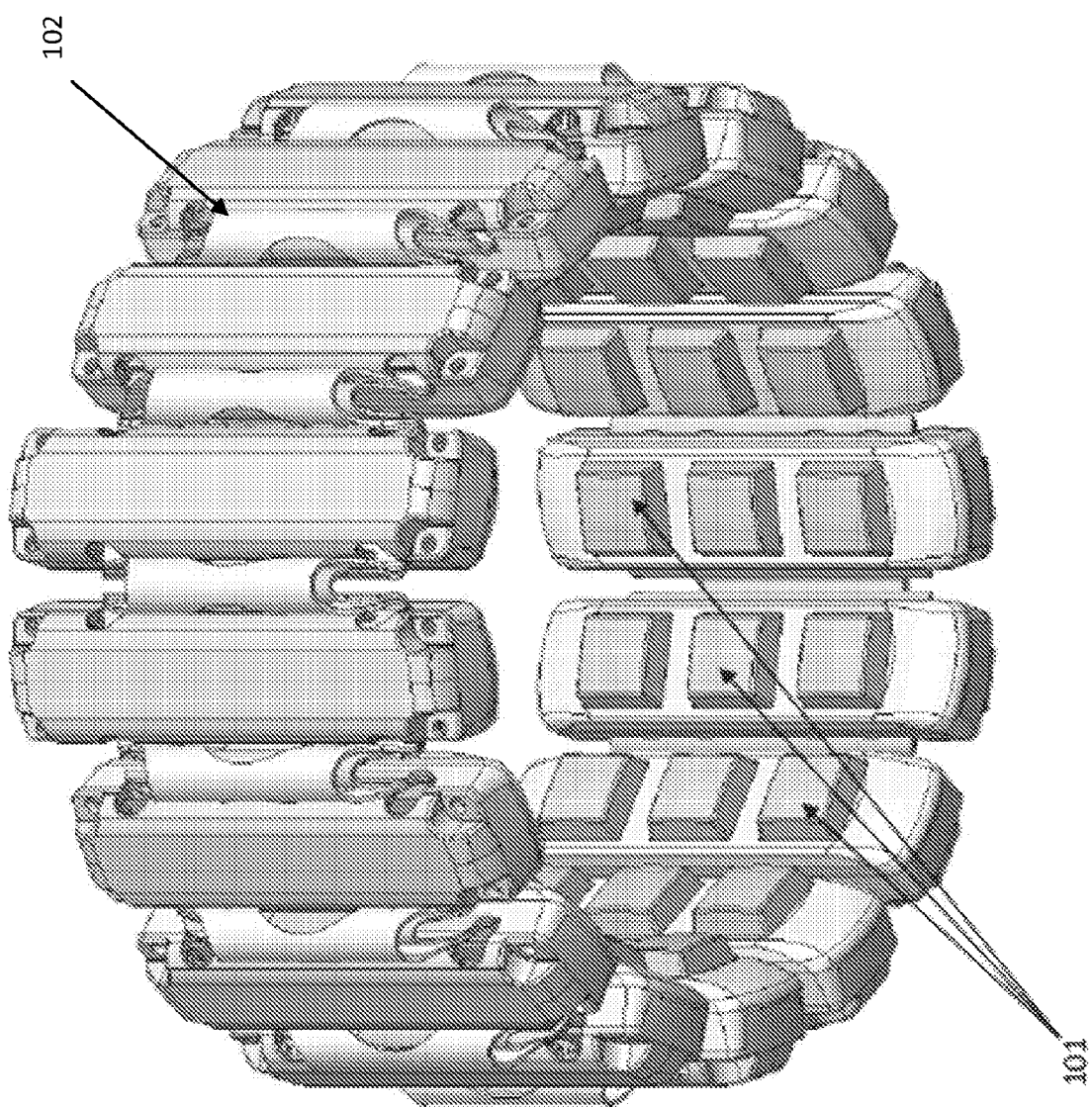
FIG. 1 illustrates a wearable system with sixteen EMG sensors arranged circumferentially around a band configured to be worn around a user's lower arm or wrist, in accordance with some embodiments of the technology described herein.

The disclosed methods and apparatus herein relate to autocalibration of sensor systems such that the systems perform well when the sensors are worn by users in various orientations and/or locations on a body part In some embodiments of the technology described herein, sensor signals may be used to predict information about a position and/or a movement of one or more portions of a user's body (e.g., a leg, an arm, and/or a hand), which may be represented as a multi-segment articulated rigid-body system with joints connecting the multiple segments of the rigid-body system. For example, in the case of a hand movement, signals sensed by wearable neuromuscular sensors placed at locations on the user's body (e.g., the user's arm and/or wrist) may be provided as input to one or more inference models trained to predict estimates of the position (e.g., absolute position, relative position, orientation) and the force(s) associated with a plurality of rigid segments in a computer-based musculoskeletal representation associated with a hand, for example, when the user performs one or more hand movements. The combination of position information and force information associated with segments of the musculoskeletal representation associated with a hand may be referred to herein as a "handstate" of the musculoskeletal representation. As a user performs different movements, a trained inference model may interpret neuromuscular signals sensed by the wearable neuromuscular sensors into position and force estimates (handstate information) that are used to update the musculoskeletal representation.

In certain embodiments, processed neuromuscular signals and/or neuromuscular signal patterns (e.g., EMG signals and/or EMG signal patterns) are collected from multiple users, and the processed signals and/or signal patterns are used to generate generalized models to predict the orientation and/or location of an armband containing EMG sensors. For example, spatiotemporal patterns of EMG signals can be obtained as users perform different handstate configurations with or without system supervision (e.g., gestures or poses comprising various pinches and wrist movements in the four cardinal directions) when the armband is positioned on the forearm and/or oriented in various ways, and these signals can be used to train generalized inference models to predict the user's gestures based on detected EMG signals. In certain embodiments, the systems and methods disclosed herein comprise identifying a "virtual" reference electrode and mapping the specific orientation of an armband to an offset value associated with an electrode and the "virtual" reference electrode.

As used herein, the term "gestures" may refer to a static or dynamic configuration of one or more body parts including a position of the one or more body parts and forces associated with the configuration. For example, gestures may include discrete gestures, such as placing or pressing the palm of a hand down on a solid surface, or grasping a ball, or pinching two fingers together (e.g., to form a pose); or continuous gestures, such as waving a finger back and forth, grasping and throwing a ball, rotating a wrist in a direction; or a combination of discrete and continuous gestures. Gestures may include covert gestures that may be imperceptible to another person, such as slightly tensing a joint by co-contracting opposing muscles or using sub-muscular activations, or "off-manifold" activations. In training an inference model, gestures may be defined using an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

Following autocalibration of the system(s), in various embodiments, a number of muscular activation states of a user may be identified from the recorded and/or detected signals and/or information based on the signals, to enable improved selection and/or control of objects in the user's environment when those objects are configured to receive control signals. The control of the objects can be performed directly from a neuromuscular activity device or indirectly via another system such as an augmented reality (AR) system or any extended or cross reality system (XR system or environment), including but not limited to mixed reality (MR), virtual reality (VR), etc.

The description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It, however, will be clear and apparent that the subject technology is not limited to the specific details set forth herein and may be practiced without these specific details. In some instances, well-known structures and components are shown in block diagram form to avoid obscuring the concepts of the subject technology.

The terms "computer", "processor", "computer processor", "compute device" or the like should be expansively construed to cover any kind of electronic device with data processing capabilities including, by way of non-limiting example, a digital signal processor (DSP), a microcontroller, a field programmable gate array (FPGA), an application specific integrated circuit (ASIC), or any other electronic computing device comprising one or more processors of any kind, or any combination thereof.

As used herein, the phrase "for example," "such as", "for instance" and variants thereof describe non-limiting embodiments of the presently disclosed subject matter. Reference in the specification to "one case", "some cases", "other cases", or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

FIG. 1 illustrates a band system with sixteen EMG sensors arranged circumferentially around an elastic band 102 configured to he worn around a user's lower arm. For example, FIG. 1 shows EMG sensors 101 arranged circumferentially (e.g., symmetrically spaced) around elastic band 102. It should be appreciated that any suitable number of neuromuscular sensors may be used and the number and arrangement of neuromuscular sensors used may depend on the particular application for which the wearable device is used. For example, a wearable armband or wristband may be used to generate control information for controlling an augmented reality system, a robot, controlling a vehicle, scrolling through text, controlling a virtual avatar, or any other suitable control task. Further, the band system can be configured to he worn around other parts of a user's body, such as their thigh or calf, for example.

In some embodiments, sensors 101 only includes a plurality of neuromuscular or muscular sensors or electrodes (e.g., EMG electrodes/sensors, MMG electrodes/sensors, SMG electrodes/sensors, etc.). In other embodiments, sensors 101 includes a plurality of neuromuscular sensors and at least one "auxiliary" sensor configured to continuously record a plurality of auxiliary signals. Examples of auxiliary sensors include, but are not limited to, other sensors such as inertial measurement unit (IMU) sensors, microphones, imaging devices (e.g., a camera), radiation based sensors for use with a radiation-generation device (e.g., a laser-scanning device), or other types of sensors such as a heart-rate monitor.

In some embodiments, the output of one or more of the sensors may be optionally processed using hardware signal processing circuitry (e.g., to perform amplification, filtering, and/or rectification). In other embodiments, at least one signal processing of the output of the sensors may be performed in software. Thus, signal processing of signals sensed by the sensors may be performed in hardware, software, or by any suitable combination of hardware and software, as aspects of the technology described herein are not limited in this respect. A non-limiting example of a signal-processing procedure used to process recorded data from the sensors 101 is discussed in more detail below in connection with FIGS. 2A and 2B.

Figure 2A:
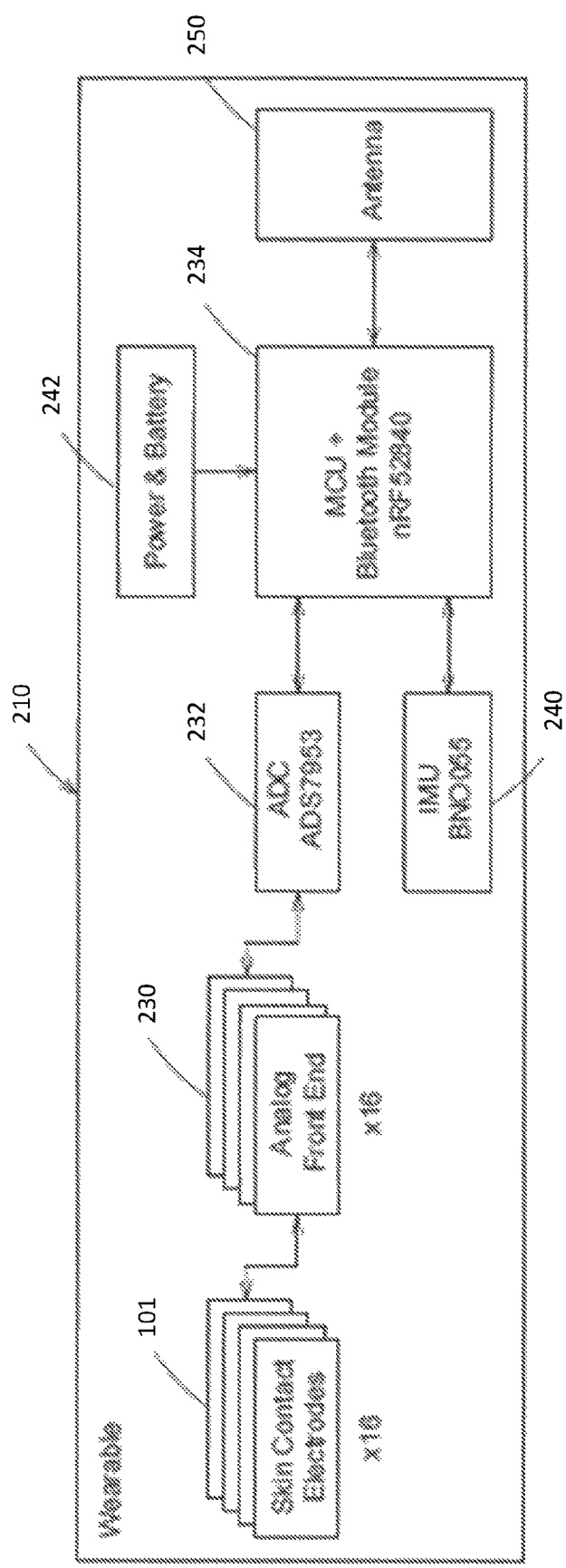
FIGS. 2A and 2B schematically illustrate a computer-based system that includes a wearable portion and a dongle portion, respectively, in accordance with some embodiments of the technology described herein.
Figure 2B:
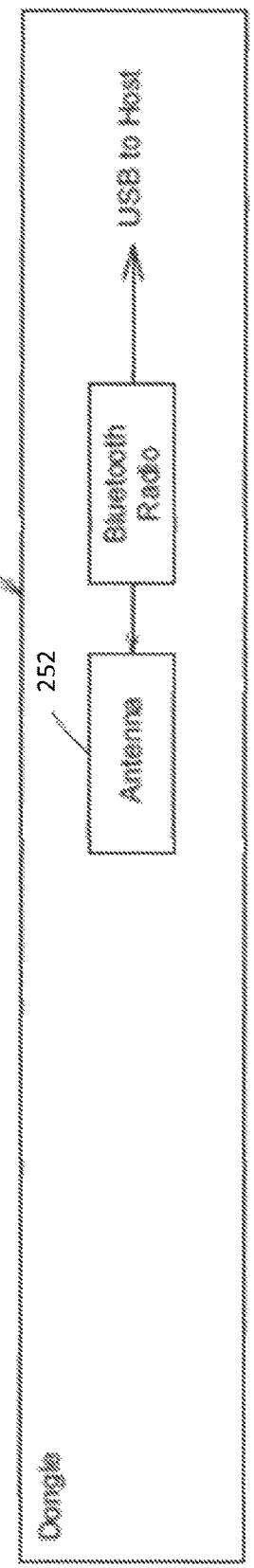

FIGS. 2A and 2B illustrate a schematic diagram with internal components of a wearable system with sixteen sensors (e.g., EMG sensors), in accordance with some embodiments of the technology described herein. As shown, the wearable system includes a wearable portion 210 (FIG. 2A) and a dongle portion 220 (FIG. 2B). Although not illustrated, the dongle portion 220 is in communication with the wearable portion 210 (e.g., via Bluetooth or another suitable short range wireless communication technology). As shown in FIG. 2A, the wearable portion 210 includes the sensors 101, examples of which are described above in connection with FIG. 1. The sensors 101 provide output (e.g., sensed signals) to an analog front end 230, which performs analog processing (e.g., noise reduction, filtering, etc.) on the sensed signals. Processed analog signals produced by the analog front end 230 are then provided to an analog-to-digital converter 232, which converts the processed analog signals to digital signals that can be processed by one or more computer processors. An example of a computer processor that may be used in accordance with some embodiments is a microcontroller (MCU) 234. As shown in FIG. 2A, the MCU 234 may also receive inputs from other sensors (e.g., an IMU 240) and from a power and battery module 242. As will be appreciated, the MCU 234 may receive data from other devices not specifically shown. A processing output by the MCU 234 may be provided to an antenna 250 for transmission to the dongle portion 220, shown in FIG. 2B.

The dongle portion 220 includes an antenna 252 that communicates with the antenna 250 of the wearable portion 210. Communication between the antennas 250 and 252 may occur using any suitable wireless technology and protocol, non-limiting examples of which include radiofrequency signaling and Bluetooth. As shown, the signals received by the antenna 252 of the dongle portion 220 may be provided to a host computer for further processing, for display, and/or for effecting control of a particular physical or virtual object or objects (e.g., to perform a control operation in an AR or VR environment)

Although the examples provided with reference to FIGS. 1, 2A, and 2B are discussed in the context of interfaces with EMG sensors, it is to be understood that the wearable systems described herein can also be implemented with other types of sensors, including, but not limited to, mechanomyography (MMG) sensors, sonomyography (SMG) sensors, and electrical impedance tomography (EIT) sensors.

As described above in connection with FIGS. 2A and 2B, the wearable system may include one or more computer processors (e.g., MCU 234) programmed to communicate with the sensors (e.g., neuromuscular sensors 101 and/or IMU sensor(s) 240). For example, signals recorded by one or more of the sensors may be provided to the processor(s), which may be programmed to execute one or more trained inference models or machine learning models that process signals captured by the sensors.

In some embodiments, the trained inference model(s) may comprise a neural network and, for example, may comprise a recurrent neural network. In some embodiments, the recurrent neural network may be a long short-term memory (LSTM) neural network. It should be appreciated, however, that the recurrent neural network is not limited to be an LSTM neural network and may have any other suitable architecture. For example, in some embodiments, the recurrent neural network may be a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used. In some implementations, the inference model(s) can comprise an unsupervised machine learning model, i.e., users are not required to perform a predetermined set of handstate configurations for which an inference model was previously trained to predict or identify. In other embodiments, the inference model(s) can comprise one or more supervised machine learning models wherein users performed specific gestures or handstate configurations in response to instructions, and the detected and processed signals from the electrodes or sensors have been associated with the performed gestures or handstate configurations.

In some embodiments, one or more inference models (e.g., a neural network as discussed above) can be implemented to classify sets of EMG signals or patterns characterized by unique spatio-temporal patterns that vary in amplitude for different amounts of forces generated by users' muscles or motor units. The processed EMG signals and/or patterns can be associated with a manner or way a user wears the band system during signal sensing (e.g., the orientation and/or positioning of the band on user's forearm). Accordingly, in one embodiment, the inference model(s) can associate one or more unique EMG signals or patterns with a specific orientation and/or location of the neuromuscular armband on the user (e.g., in a manner in which the electrodes are in contact with certain areas of the user's skin). Likewise, the inference model(s) can associate one or more unique EMG signals or patterns with a rotated orientation of the armband and/or with a re-located positioning of the armband when the user moves the armband from a lower forearm position to an upper forearm position (or the other way around, i.e., from an upper forearm position to a lower forearm position). Thus, the inference model(s) can be trained to associate various armband rotations and/or positional offsets with detected and processed EMG signals or signal patterns. Once the system can identify the specific orientation and/or positioning of the band on the user, the system can select and apply one or more previously-trained inference model(s) at that specific orientation and/or positioning in order to predict, for example, user handstate configurations with a higher level of accuracy compared to other inference model(s) that may have been previously trained using different orientations and/or positions of the band on users. Differently stated, in certain embodiments, the armband system can be calibrated via selection of particular inference model(s) such that the system adapts to any rotation and/or arm position offset without interfering with the user experience, also referred to herein as autocalibration. In other embodiments, the detected offset in orientation and/or relative difference in location of the band on the user compared to the orientation and/or positioning of the band used to train one or more inference models can be used to "normalize" the orientation and/or location of the band for input into the inference model(s). A virtual reference electrode (e.g., the "0" electrode) may be defined, and a rotation offset relative to the virtual reference electrode may be used to normalize the orientation and/or location of the band. For example, it may be determined based on the detected and processed EMG signals that the band has a rotational offset of three electrodes from the virtual reference electrode. In such an instance, the detected EMG signals can be further processed to account for this particular offset (either before or after being input into the trained inference models).

In some implementations, the armband system can be autocalibrated such that, the armband system adapts to users that may have injured or missing muscles, different adipose tissue or fat, and other anatomic variables. Although discussed below in the context of multiple trained inference models, it is appreciated that the embodiments discussed herein can in some instances be implemented as a single or sole trained inference model or machine learning model. It is also appreciated that at least some of the inference models may be trained from data collected from multiple users. For instance, data can be collected from recorded EMG signals of multiple users while they perform one or more handstate configurations, e.g., poses or gestures.

In one embodiment, the inference model that classifies EMG patterns can be created as follows: 1) build a new inference model/experiment class that takes as input(s) a set of preprocessed EMG signals; 2) generate training data by randomly applying a rotation offset to the preprocessed EMG signals; 3) produce positive labels when the augmented offset is 0, and null otherwise; 4) calibrate the training data to have calibrated data at offset=0; and 5) train an inference model using the calibrated training data, and evaluate the performance of the trained inference model by testing different rotation offsets.

Figure 3:
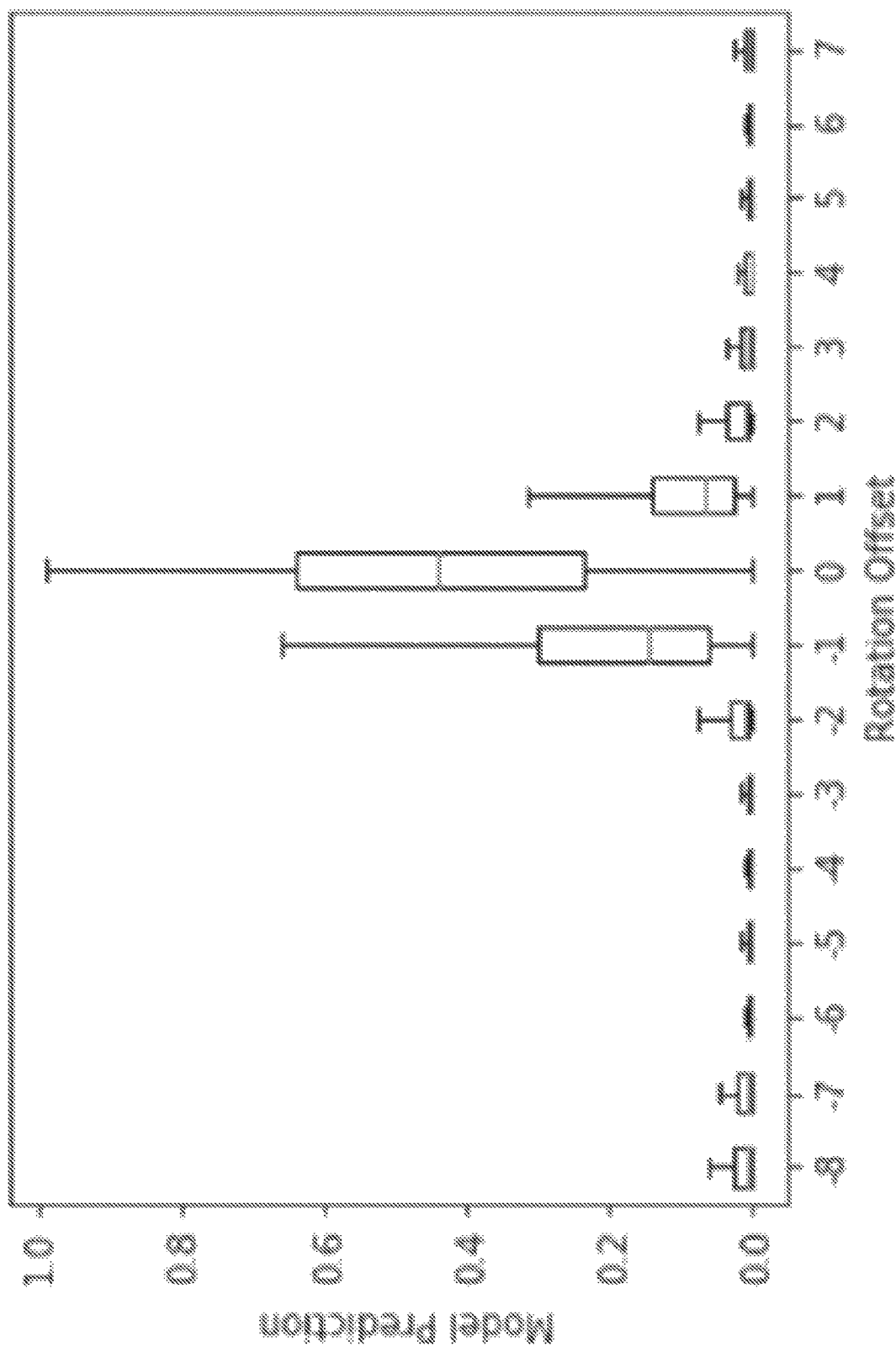
FIG. 3 is a plot illustrating an example distribution of outputs generated by an autocalibration model trained in accordance with some embodiments. The distribution of outputs is generated across a dataset with data collected from different users.
Figure 4:
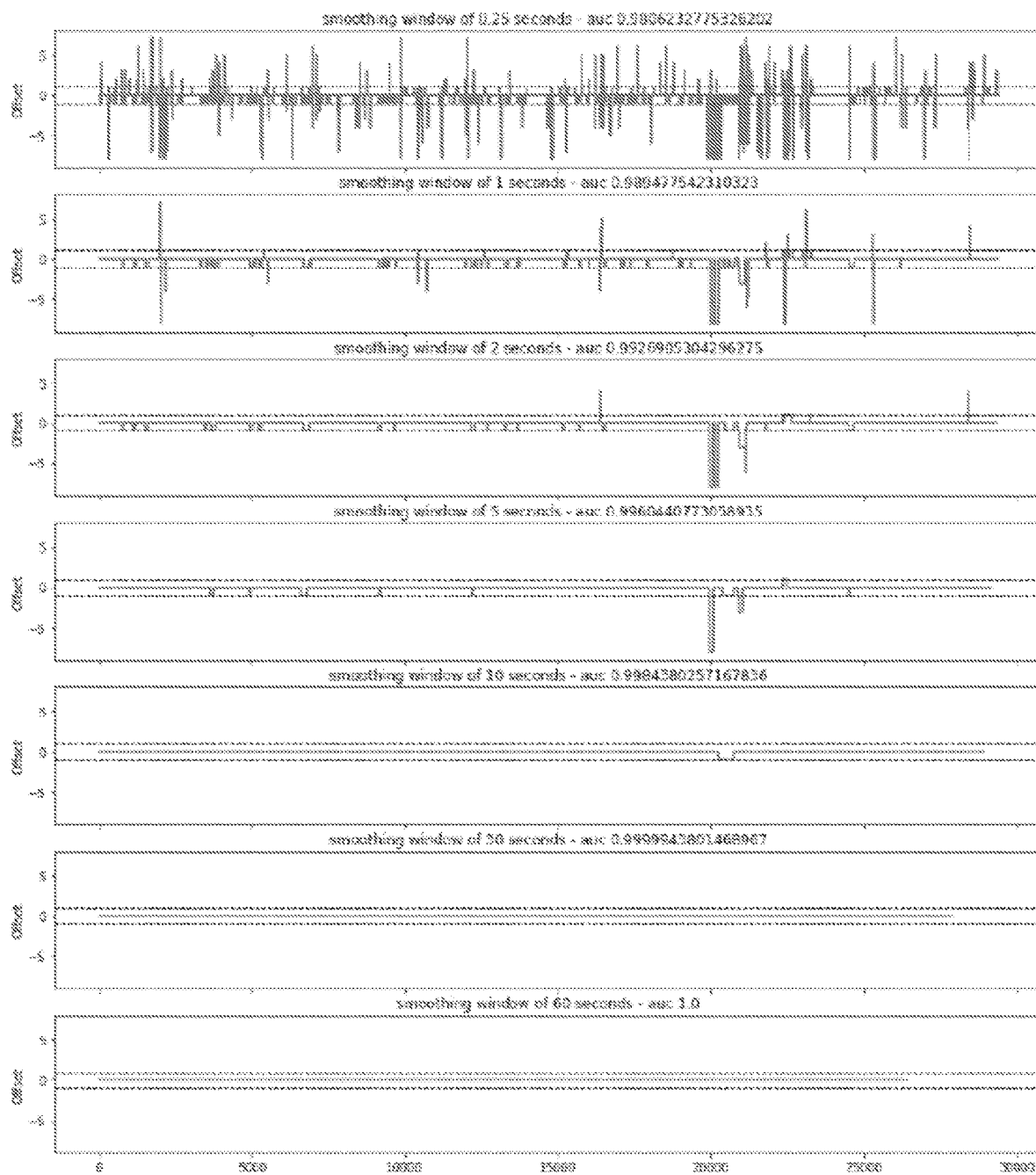
FIG. 4 shows predicted values output from an autocalibration model trained in accordance with some embodiments. The predicted value are averaged across time which result in model predictions with greater confidence values.
Figure 5:
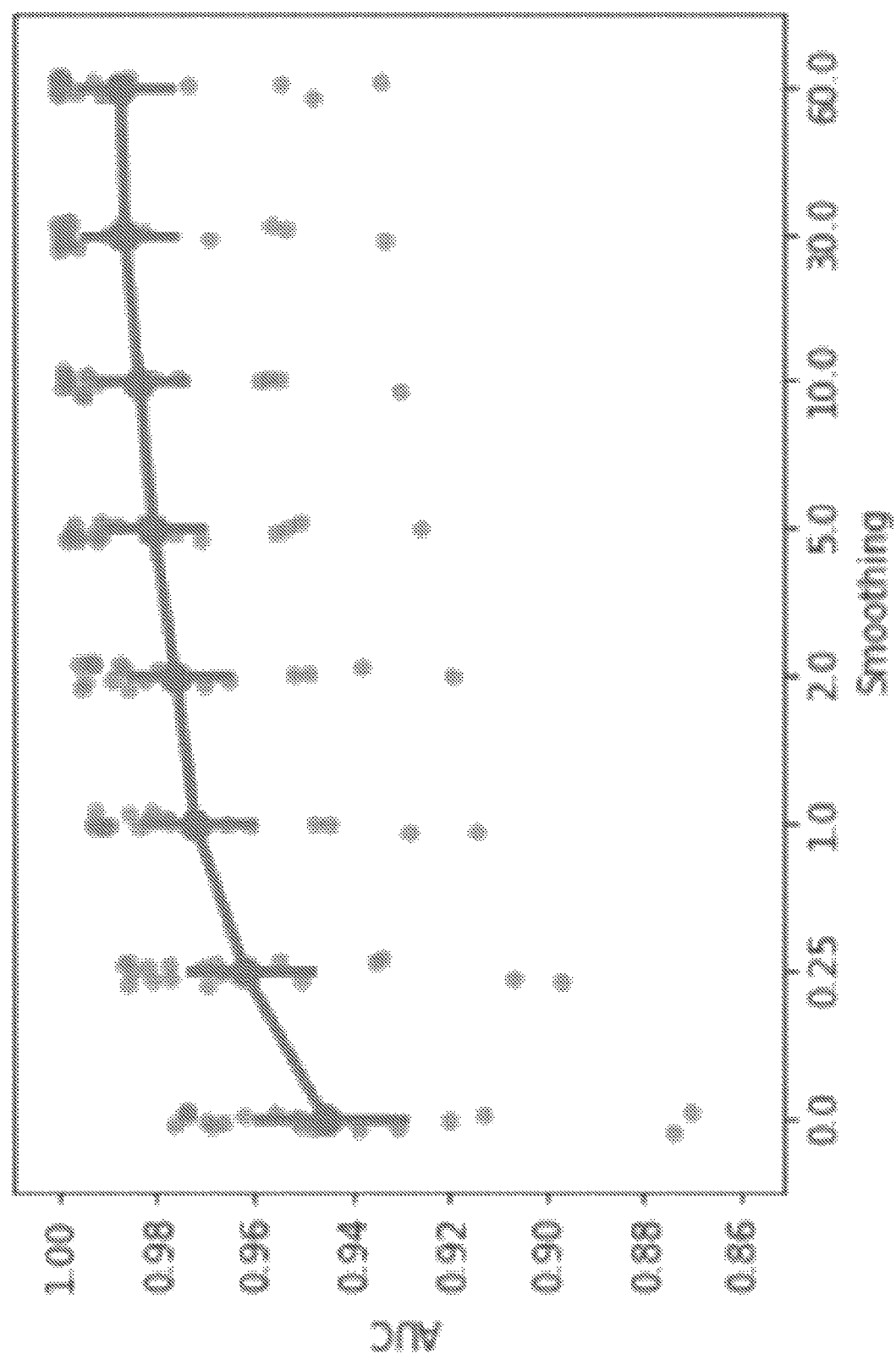
FIG. 5 shows a plot of the accuracy of an autocalibration model trained in accordance with some embodiments. The accuracy is expressed in an Area Under the Receiver Operating Characteristic Curve (AUC)

An example of a distribution of outputs generated by a trained inference model across a dataset with data collected from different users is shown in FIG. 3. It can be appreciated that on average the trained model outputs show higher confidence values when the training data is calibrated (i.e., offset=0) compared to when the training data is not calibrated. In this example, the trained model produces a prediction for every 80 millisecond (ms) chunk of collected EMG data, however, other time intervals can be analogously used. Also, in this example, a binary classifier is used to determine whether the band is calibrated at the "0" electrode in the preferred orientation. FIG. 4 shows predicted values averaged across time which result in predictions with greater confidence values. It can be appreciated that by applying a smoothing factor of 10 seconds the predicted offset can be acquired with more accuracy e.g., an accuracy at the ±1 electrode range. FIG. 5 shows the accuracy of the model expressed in Area Under the Receiver Operating Characteristic Curve (AUC).

Figure 6:
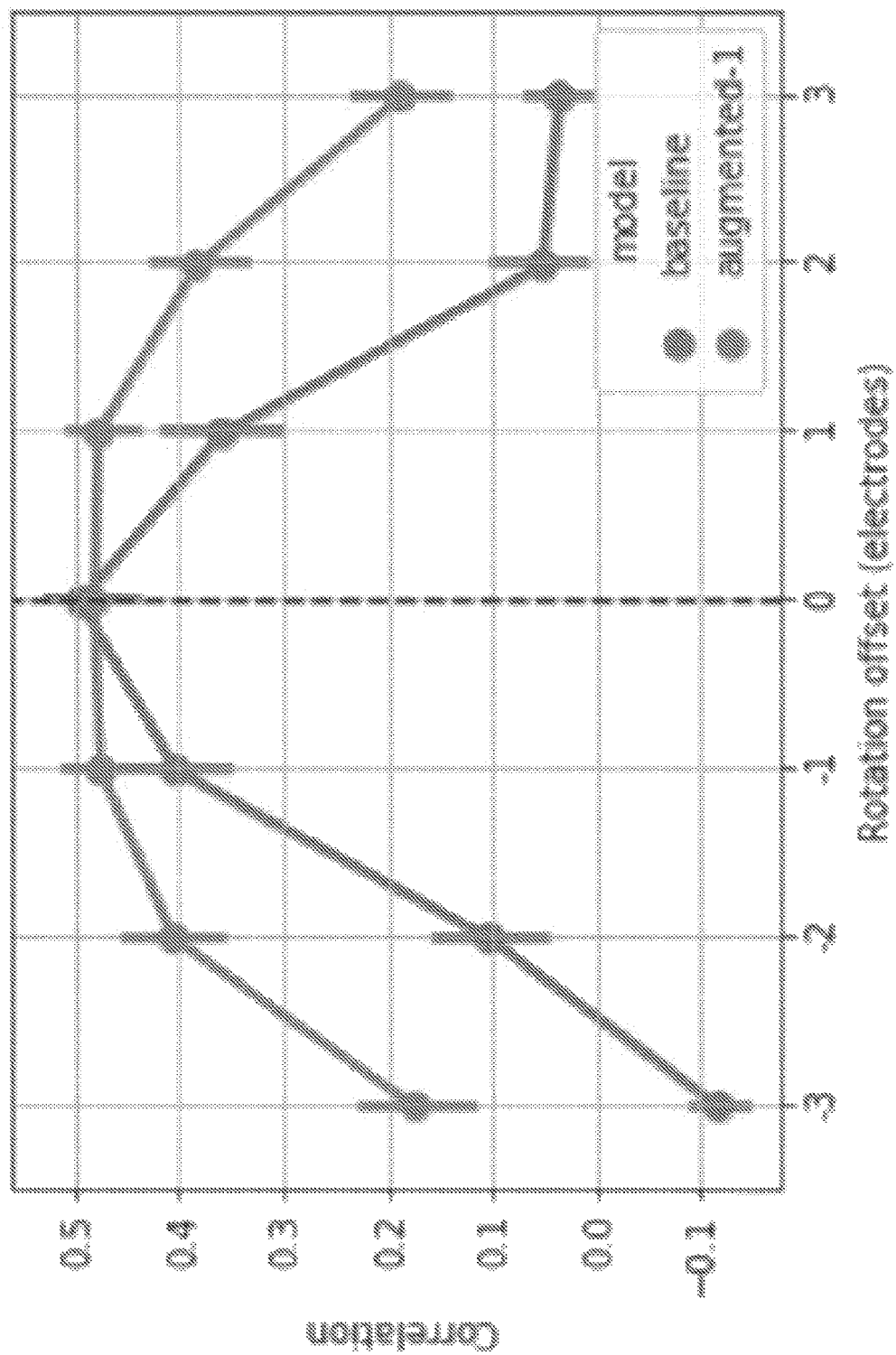
FIG. 6 shows a plot of a correlation between a baseline model and an augmented model for autocalibrating sensors of a wearable device in accordance with some embodiments.
Figure 7:
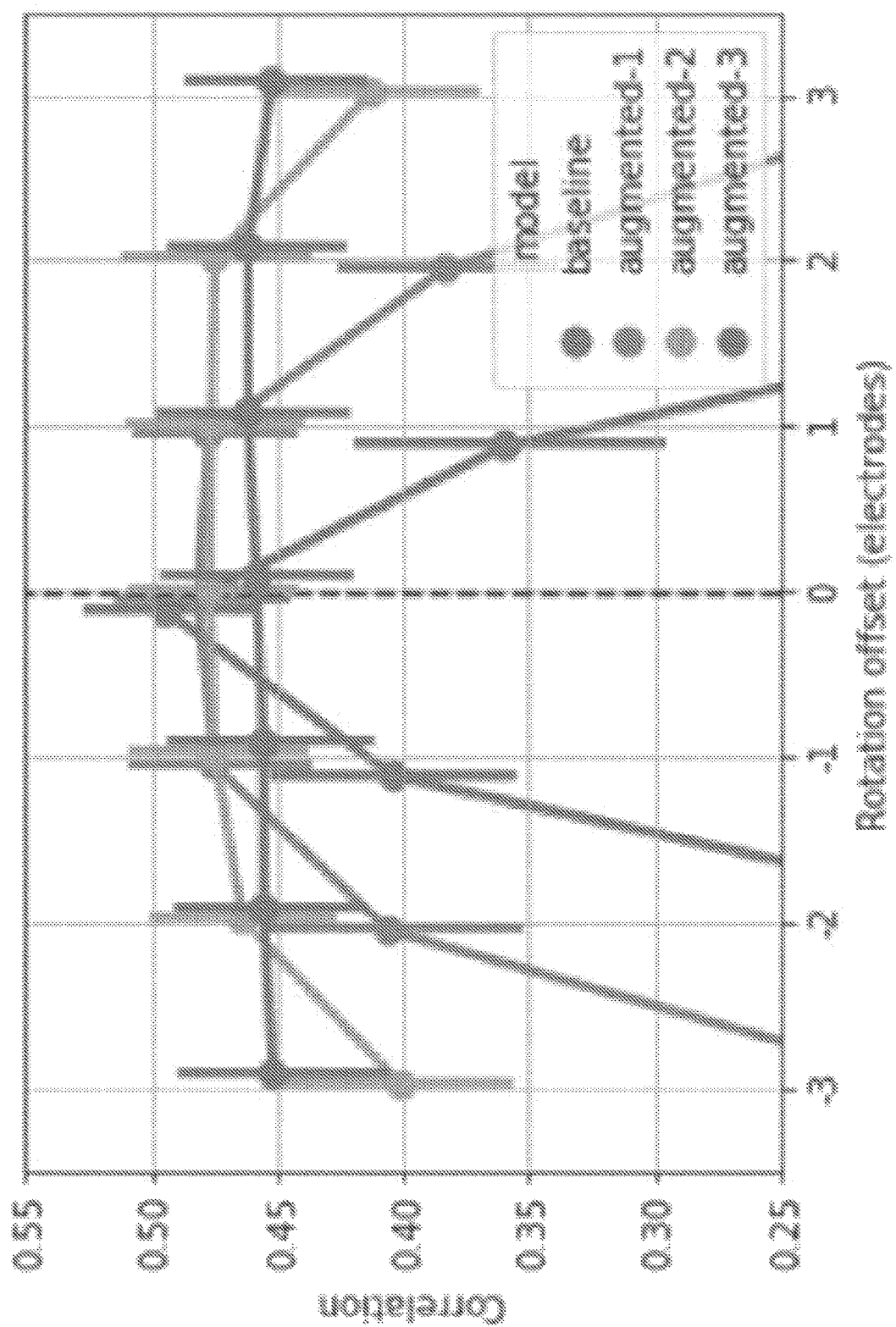
FIG. 7 shows a plot of correlations of augmented inference models trained with electrode invariances set to ±1, ±2, and ±3 along with the baseline model in accordance with some embodiments.

In some implementations, an electrode invariance factor associated with a small offset error can be provided as an input to an inference model, e.g., during the training phase. Such an inference model is also referred herein as an augmented inference model. The augmented inference model can be implemented by, for instance, expanding a batch of training data and creating a new dimension for each sample in a training data batch. The new dimension includes concatenations of different versions of the same feature vector with different electrode rotations. For example, given a feature vector of dimension 384, an invariance of ±1 electrode can be set by providing as input to the augmented inference model a feature tensor of dimension 3×384. Such a feature tensor includes the extra dimension containing the same feature vector with the three rotation offsets [−1, 0, 1]. Then, the augmented inference model may be initiated with a first input dense layer and this extra dimension may be reduced by pooling across the extra dimension, for instance, by taking the maximum activation over the extra dimension. Accordingly, the augmented inference model applies the same set of coefficients (for the first dense layer) for each of the three offsets, then selects for each filter the largest activation over the three proposed offsets. FIG. 6 illustrates a correlation between a baseline model and the augmented inference model. It should be appreciated that the baseline model is more sensitive to the offset errors, as it sharply drops performance when is not calibrated (i.e., offset !=0). FIG. 7 illustrates correlations of augmented inference models trained with electrode invariances set to ±1, ±2, and ±3 along with the baseline model.

Figure 8:
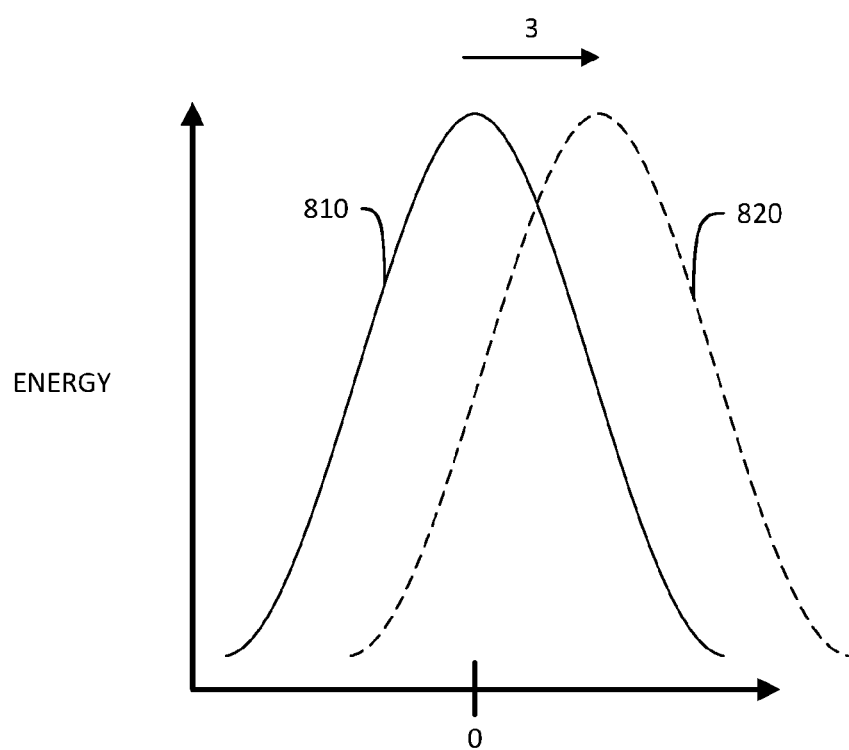
FIG. 8 schematically illustrates a visualization of an energy plot for a single EMG electrode on a wearable device at a first position and a second position in which the wearable device has been rotated.

In another embodiment, the autocalibration process comprises numerically aligning the band position (e.g., rotation, location on the forearm, and/or orientation) via common reference point(s) across different users and their forearms and/or wrists, so that the system can identify virtual reference point(s) for each electrode and can consistently represent the same part of the forearm and/or wrist irrespective of the band position. For example, this can be done by applying an electrode permutation (e.g., reversing the order of the electrodes depending on the band orientation as applied to the forearm, or as applied to the left or right forearms) and applying a circular rotation to the electrodes. FIG. 8 schematically shows a visualization of an energy plot for a single EMG electrode "0" at a first position 810, and at a second position 820 in which the EMG electrode is rotated three positions. The disclosed systems and methods herein can utilize the difference(s) in such energy plots in order to achieve the autocalibration results as described herein.

In some embodiments, the user need not perform a specific calibration gesture to register the band position. Instead, an autocalibration model can be trained to recognize and predict the specific electrode permutation that generated a given set of EMG signals or patterns. Data augmentation techniques can be implemented on data sets obtained in a supervised machine learning fashion. For example, offline EMG data can be collected from a set of users who performed a set of canonical gestures or poses comprising various pinches and wrist movements in the four cardinal directions to register the band rotations based on the collected and processed EMG data associated with those gestures or poses. With this process, the system can generate labels to train a model (e.g., an autocalibration model) to recognize different simulated band rotations and/or orientations (e.g., data augmentation). The number of gestures or poses upon which the autocalibration model is trained can vary, but may comprise approximately eight gestures. In this embodiment, the autocalibration task can be regarded as a classification task, and more collected and labeled data may lead to better precision on the predicted offset of the electrode(s). During this offline training, the band can be rotated and additional data can be collected from users in each of the rotated positions. For example, if the band has 16 electrode channels, data can be collected from the same user or across multiple users at each of 16 different orientations. Some embodiments employ an autocalibration model to predict that the wearable system is rotated into one of multiple (e.g., 16) positions.

Figure 9:
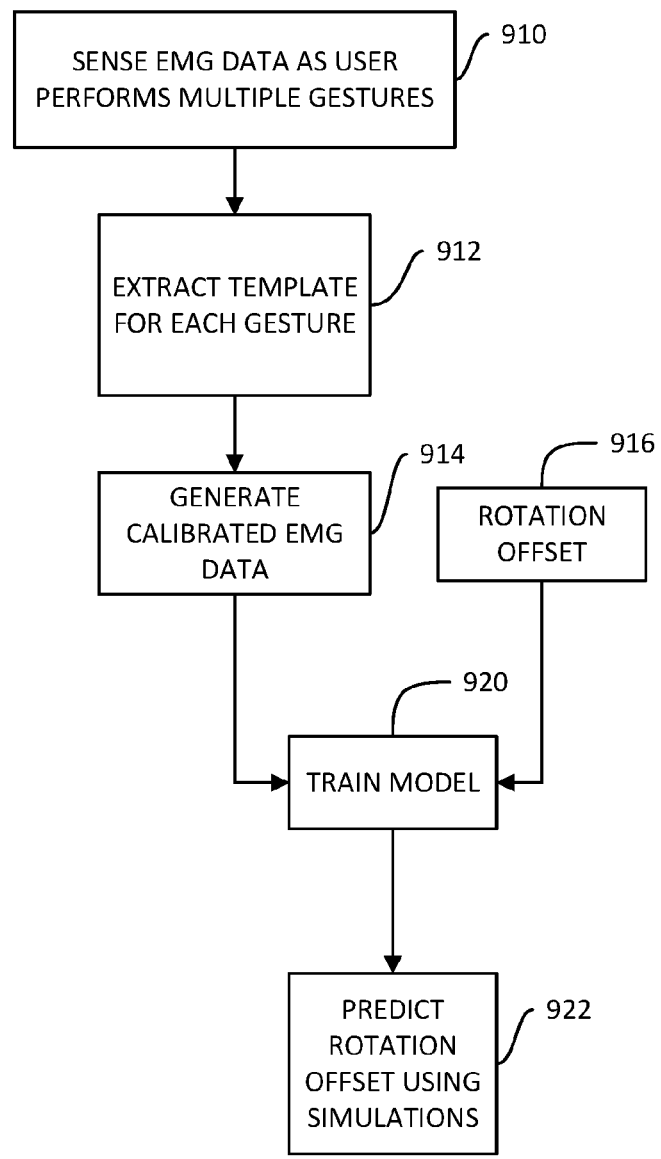
FIG. 9 illustrates a flowchart of a process for offline training of an autocalibration model based on neuromuscular signals recorded from a plurality of users in accordance with some embodiments.

FIG. 9 shows an example of a flowchart for offline training of an autocalibration model in accordance with some embodiments. In act 910 EMG data is sensed as one or more users are performing multiple gestures or poses with different band orientations. As discussed above, any suitable number of gestures or poses (e.g., 8 gestures or poses) may be used. The process then proceeds to act 912, where templates are extracted for each gesture or pose, wherein each of the templates corresponds to spatio-temporal patterns of the sensed EMG signals. The process then proceeds to act 914, where the extracted templates are used to generate calibrated EMG data. Any given electrode channel can he designated the "0" channel electrode at which the system is set to by default process and interpret EMG inputs to predict handstate configurations.

In act 916, each of the band orientations during data collection is assigned an offset value depending on the degree of rotation of the armband when the data was collected. In this way, each labeled data set collected and processed for the specific gestures and/or poses can be further be labeled with an offset value depending on the band orientation and associated simulation position can be generated for the band. The labeled data for calibrated EMG signals, which have been assigned to gestures and/or poses, and EMG signals identified based on specific electrode channel orientation(s) can be input into an autocalibration model in act 920 to train the model. In some embodiments, the autocalibration model is a neural network (such as an LSTM, for example), and the autocalibration model is trained to predict the orientation of the armband based on received EMG signal data. Once properly trained, the process proceeds to act 922 where the autocalibration model can be implemented for any user to predict the orientation and/or rotation offset of the band (e.g., with respect to the "0" channel) based on received EMG data from the user and simulations of the band positioning and/or orientation based on previously-collected user EMG data. In some embodiments, the model may be trained such that it can predict the degree of rotation or offset to an error of +/−1 electrode channel.

After the autocalibration model has been suitably trained to predict the orientation of the band within an error of +/−1 electrode channel, the autocalibration model can be used "online" to predict the band orientation on any given user during the user's performance of one or more motor actions or intended motor actions.

Figure 10:
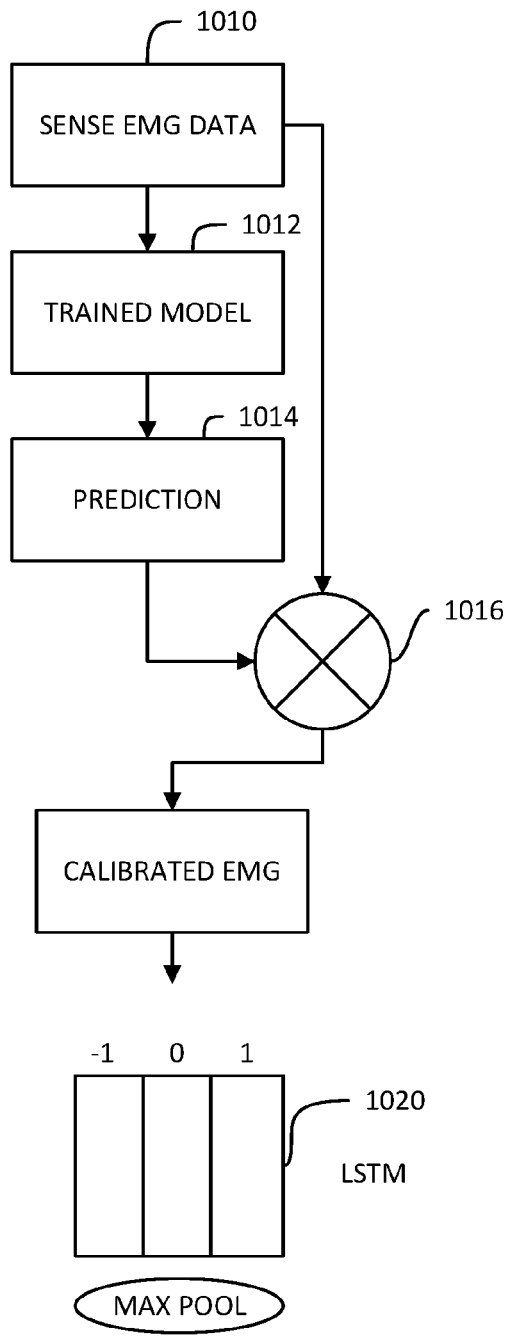
FIG. 10 illustrates a flowchart of a process for using the trained autocalibration model to calibrate the position and/or orientation of sensors on a wearable device in accordance with some embodiments.

By contrast to techniques that require the user to perform a specific gesture or pose for calibration, some embodiments use autocalibration to automatically detect the position of the wearable device on a body part using an autocalibration model that does not require the user to perform a specific calibration gesture or pose. Such embodiments permit continuous or periodic autocalibration of the device as the user wears the device without requiring the user to stop what they are doing and perform a particular calibration gesture or pose. FIG. 10 illustrates a flowchart for online usage of a trained autocalibration model in accordance with some embodiments. In act 1010, EMG data is sensed from a user wearing the wearable device (e.g., the wearable device shown in FIG. 1). In act 1012, the sensed EMG data is provided to a trained autocalibration model (e.g., the autocalibration model trained in act 920 of the process in FIG. 9). The process of FIG. 10 then proceeds to act 1014 where the output of the model is used to predict a position and/or orientation of the wearable device by, for example, classifying the EMG signal or signal patterns into one of multiple (e.g., 16) rotation positions. The process then proceeds to act 1016 where a correction based on the predicted output of the autocalibration model is applied to the sensed EMG data to generate calibrated EMG data. In other embodiments, the sensed EMG data is not corrected, and the sensed EMG data is provided as input to selected inferential models trained at the detected orientation(s) and/or position(s) or provided as input to models that have been modified to interpret the sensed EMG data and accurately output handstate configurations, poses. and/or gestures.

As described above, in some embodiments, the autocalibration model may be implemented as an LSTM neural network. In certain embodiments, it is desirable to address the +/−1 electrode channel error rate for the rotation offset (see FIG. 6 showing an augmented model performing equally well for +/−1 electrode offset, but the baseline model performing not as well for a +/−1 electrode offset). This can be done by implementing a pooling layer within the neural network as shown schematically in act 1020 of FIG. 10. For example, the pooling layer may be a max pooling layer where the max pooling layer can be configured to determine the location of the "0" electrode channel (e.g., based on a probabilistic calculation for each of the three electrode locations), so the system can virtually label a specific electrode channel as the "0" reference channel out of a possible set of three channels initially identified by the autocalibration model. It should be understood that other types of pooling layers can be used that are well known in the art, e.g., average or mean pooling layers.

In certain embodiments, the band detects and analyzes EMG signals or EMG signal patterns either continuously for a certain period of time or at discrete time points. In either case, during this defined period of time or at discrete time points, the autocalibration model(s) can be used to determine the orientation and/or positioning of the band on the user's body part. e.g., forearm. In certain embodiments, the band detects and processes EMG signals or EMG signal patterns initially upon the user putting the band on and/or in response to detecting band movement subsequent to initial placement of the band. For example, the system may identify that at least a portion of the wearable device (e.g., one or more EMG sensors) has moved, e.g., rotated around and/or translated along the wrist or forearm of the user, and in response to determining that the at least a portion of the wearable device (e.g., the band) has moved, the system may perform autocalibration by determining a current position and/or orientation of the wearable device in accordance with one or more of the autocalibration techniques described herein. By automatically restarting calibration after identifying movement of the wearable device, re-calibration can be performed in an efficient and timely manner.

Movement of the wearable device on the user can be detected in any suitable manner. In some embodiments. detection of movement of the wearable device is based on one or more detected movement artifacts identified in the neuromuscular signals sensed by the plurality of neuromuscular sensors. In other embodiments that include at least one inertial measurement unit (IMU) sensor, movement of the wearable device may be detected based at least in part, on at least one signal sensed by the at least one IMU sensor. In yet other embodiments, detection of movement of the wearable device may be based, at least in part, on signals from multiple types of sensors (e.g., at least one EMG sensor and at least one IMU sensor) and/or sensors included on or external to the wearable device (e.g., at least one camera sensor).

Using the techniques described herein, the system may he able to calibrate the orientation and/or position of the armband in less than 10 seconds based on one or more sampling rates or frequencies. In other embodiments, due to settling time of the EMG electrodes (e.g., from skin-electrode interactions) after band movements, which can lead to an initially degraded signal quality, it may take a little longer to get a reliable estimation of the band position. For example, the system can initiate an autocalibration sequence upon detection of band movement, and the sequence can run for approximately 30 seconds to get a more reliable prediction of band orientation and/or position. Shorter time periods can be used to run the autocalibration sequences provided that the settling time can he reduced and little to no band movement is detected during the autocalibration sequence. In certain embodiments, the autocalibration sequence can be initiated and re-run upon the detection of any band movements no matter how slight in order to maximize the accuracy of the predictions associated with EMG signals or EMG signal patterns.

In other embodiments, the techniques described herein can be used to identify a specific position on the user's body part, e.g., how far up the band is sitting on the user's forearm as it relates to the distances between the band and the user's elbow joint or wrist joint. Similar to the embodiment described above (e.g., in FIG. 9) in which a generalized, offline model is generated and trained from labeled EMG signal or EMG signal pattern data with users performing different gestures and/or poses at different orientations of the band, in other embodiments additional data can be collected from users performing gestures and/or poses at different or the same orientations of the band but at different positions on the user's body part (e.g., along portions of the forearm). In this way, one or more generalized models can be trained to predict not only the specific orientation (e.g., rotation) of the band, but also its positioning on the user's body part (e.g., relative to a reference point such as the elbow joint or wrist joint). Such embodiments can be used to better predict user handstate configurations given potential variability in EMG signals or EMG signal patterns depending on the specific location of the band on the user. Given neuroanatomical constraints and specific user neuroanatomy, it may be advantageous to analyze EMG signals on more distal or more proximal points of the user's body part (e.g., along different portions of the forearm or wrist). In certain embodiments, the autocalibration model can detect a specific positioning of the band on the user's forearm, and generate an input signal to an interface to instruct the user to reposition the band in a more distal or more proximal location depending on the specific outcome desired (e.g., to move the band farther up the aim so that relatively more EMG data can be collected or farther down the arm because certain input models to be used were trained on collected data from users with the hand closer to their wrists).

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made. Additionally, certain of the steps may be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein. Furthermore, although various embodiments are described as having a particular entity associated with a particular compute device, in other embodiments different entities can be associated with other and/or different compute devices.

It is intended that the systems and methods described herein can be performed by software (stored in memory and/or executed on hardware), hardware, or a combination thereof. Hardware modules may include, for example, a general-purpose processor, a field programmable gates array (FPGA), and/or an application specific integrated circuit (ASIC). Software modules (executed on hardware) can be expressed in a variety of software languages (e.g., computer code), including Unix utilities, C, C++, Java™, JavaScript, Ruby, SQL, SAS®, Python, Fortran, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code. Each of the devices described herein can include one or more processors as described above.

Some embodiments described herein relate to devices with a non-transitory computer-readable medium (also can be referred to as a non-transitory processor-readable medium or memory) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can he referred to as code) may he those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Processor-executable instructions can be in many forms, such as program modules, executed by one or more compute devices, and can include routines, programs, objects, components, data structures, etc. that perform particular tasks or implement particular data types, and the functionality can be combined and/or distributed as appropriate for various embodiments. Data structures can be stored in processor-readable media in a number of suitable forms. For simplicity of illustration, data structures may be shown to have fields that are related through location in the data structure. Such relationships may likewise be achieved by assigning storage for the fields with locations in a processor-readable medium that conveys relationship(s) between the fields. However, any suitable mechanism/tool can be used to establish a relationship between information in fields of a data structure, including through the use of pointers, tags or other mechanisms/tools that establish relationship between data elements.

Various disclosed concepts can be embodied as one or more methods, of which examples have been provided. The acts performed as part of a particular method can be ordered in any suitable way. Accordingly, embodiments can be constructed in which acts are performed in an order different than illustrated/discussed, which can include performing some acts simultaneously, even though shown as sequential acts in illustrative embodiments. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically malleable and/or physically interacting components and/or wirelessly interactable and/or wirelessly interacting components and/or logically interacting and/or logically interactable components.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements. should be understood to mean at least one element selected from any one or more of the elements in the list of elements, but not necessarily including at least one of each and every element specifically listed within the list of elements and not excluding any combinations of elements in the list of elements. This definition also allows that elements may optionally he present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system comprising:
    a plurality of sensors arranged on a wearable device including one or more electrodes arranged in a specified order, wherein the plurality of sensors are configured to sense a plurality of neuromuscular signals from a body part of the user; and
    at least one computer processor programmed to:
    define a virtual reference electrode among the electrodes of the wearable device;
    determine a rotation offset relative to the virtual reference electrode;
    provide the plurality of neuromuscular signals and/or signals derived from the plurality of neuromuscular signals as inputs to one or more trained autocalibration models;
    determine based, at least in part, on the output of the one or more trained autocalibration models, a current position of the wearable device on the user, wherein the orientation is established at least partially based on the determined rotation offset value relative to the virtual reference electrode, and wherein the trained autocalibration models are configured to align the rotation, location, and orientation of the wearable device via reference points that represent the same portion of the body part of the user irrespective of the wearable device's position on that body part, the aligning further including:
        applying, by the processor, an electrode permutation that alters the order of the electrodes according to the orientation of the wearable device relative to the user's body part; and
        applying, by the processor, a circular rotation to the electrodes to adapt to detected rotational changes in the plurality of sensors; and
    generate a control signal based, at least in part, on the current position and/or orientation of the wearable device on the user and the plurality of neuromuscular signals.

2. The system of claim 1, wherein the at least one computer processor is programmed to determine the current position and/or orientation of the wearable device on the user without the user performing a particular pose or gesture during sensing of the plurality of neuromuscular signals.

3. The system of claim 1, wherein the at least one computer processor is programmed to process the sensed plurality of neuromuscular signals prior to providing the processed neuromuscular signals to the one or more autocalibration models.

4. The system of claim 1, wherein the at least one programmed processor is further programmed to:
    generate calibrated neuromuscular signals based, at least in part, on the current position and/or orientation of the wearable device and the plurality of neuromuscular signals, and
    wherein generating a control signal comprises generating a control signal based, at least in part, on the calibrated neuromuscular signals.

5. The system of claim 1, wherein the at least one programmed processor is further programmed to:
    select or modify one or more inference models based, at least in part, on the current position and/or orientation of the wearable device; and
    provide the plurality of neuromuscular signals as input to the selected or modified one or more inference models, and
    wherein generating a control signal is further based, at least in part, on an output of the selected or modified one or more inference models.

6. The system of claim 1, wherein the one or more autocalibration models used to determine the current position and/or orientation of the wearable device on the user include a neural network.

7. The system of claim 6, wherein the neural network is an LSTM neural network.

8. The system of claim 7, wherein the LSTM neural network includes at least one pooling layer.

9. The system of claim 8, wherein the at least one pooling layer comprises a max pooling layer.

10. The system of claim 8, wherein the at least one pooling layer provides rotation invariance of ±1 sensor locations.

11. The system of claim 1, wherein the one or more autocalibration models are trained to identify the orientation and/or location of the wearable device based on neuromuscular signals obtained from a plurality of users.

12. The system of claim 11, wherein the neuromuscular signals obtained from the plurality of users were obtained as each of the plurality of users performed a plurality of hand gestures and/or poses while the wearable device was oriented and/or positioned in multiple different configurations on a forearm and/or wrist of the user.

13. The system of claim 1, wherein the plurality of sensors comprises a plurality of electromyography (EMG) sensors.

14. The system of claim 1, wherein the at least one computer processor is further programmed to:
    identify that at least a portion of the wearable device has moved on the wrist or forearm of the user; and
    determine the current position and/or orientation of the wearable device on the user in response to identifying that at least a portion of the wearable device has moved on the wrist or forearm of the user.

15. The system of claim 14, wherein identifying the at least a portion of the wearable device has moved on the wrist or forearm of the user comprises determining that the wearable device has rotated around and/or translated along the user's wrist or forearm.

16. The system of claim 14, wherein identifying the at least a portion of the wearable device has moved on the wrist or forearm of the user comprises detecting one or more movement artifacts in the sensed plurality of neuromuscular signals.

17. The system of claim 14, further comprising at least one inertial measurement unit (IMU) sensor, and wherein identifying the at least a portion of the wearable device has moved on the wrist or forearm of the user is based, at least in part, on at least one signal sensed by the at least one IMU sensor.

18. The system of claim 1, wherein determining the current position and/or orientation of wearable device comprises determining a rotation of the wearable device relative to a virtual reference orientation of the wearable device.

19. The system of claim 1, wherein the control signal is a control signal to control one or more operations of or within a virtual reality system or an augmented reality system.

20. A method comprising:
sensing a plurality of neuromuscular signals from a body part of the user using a plurality of sensors arranged on a wearable device in a specified order, the sensors including one or more electrodes;
defining a virtual reference electrode among the electrodes of the wearable device;
determining a rotation offset relative to the virtual reference electrode;
providing the plurality of neuromuscular signals and/or signals derived from the plurality of neuromuscular signals as inputs to one or more trained autocalibration models;
determining based, at least in part, on the output of the one or more trained autocalibration models, a current position of the wearable device on the user, the orientation is established at least partially based on the determined rotation offset value relative to the virtual reference electrode, and wherein the trained autocalibration models are configured to align the rotation, location, and orientation of the wearable device via reference points that represent the same portion of the body part of the user irrespective of the wearable device's position on that body part, the aligning further including:
    applying, by the processor, an electrode permutation that alters the order of the electrodes according to the orientation of the wearable device relative to the user's body part; and
    applying, by the processor, a circular rotation to the electrodes to adapt to detected rotational changes in the plurality of sensors; and
generating a control signal based, at least in part, on the current position and/or orientation of the wearable device on the user and the plurality of neuromuscular signals.

21. The method of claim 20, wherein determining the current position and/or orientation of the wearable device comprises determining the current position and/orientation of the wearable device without the user performing a particular pose or gesture during sensing of the plurality of neuromuscular signals.

22. The method of claim 20, further comprising processing the sensed plurality of neuromuscular signals prior to providing the processed neuromuscular signals to the one or more autocalibration models.

23. The method of claim 20, further comprising:
generating calibrated neuromuscular signals based, at least in part, on the current position and/or orientation of the wearable device and the plurality of neuromuscular signals, and
wherein generating a control signal comprises generating a control signal based, at least in part, on the calibrated neuromuscular signals.

24. The method of claim 20, further comprising:
selecting or modifying one or more inference models based, at least in part, on the current position and/or orientation of the wearable device; and
providing the plurality of neuromuscular signals as input to the selected or modified one or more inference models,
wherein generating a control signal is further based, at least in part, on an output of the selected or modified one or more inference models.

25. The method of claim 20, wherein the one or more autocalibration models used to determine the current position and/or orientation of the wearable device on the user include a neural network.

26. The method of claim 20, wherein the one or more autocalibration models are trained to identify the orientation and/or location of the wearable device based on neuromuscular signals obtained from a plurality of users.

27. The method of claim 26, wherein the neuromuscular signals obtained from a plurality of users were obtained as each of the plurality of users performed a plurality of hand gestures and/or poses while the wearable device was oriented and/or positioned in multiple different configurations on a forearm and/or wrist of the user.

28. The method of claim 20, wherein determining the current position and/or orientation of wearable device comprises determining a rotation of the wearable device relative to a virtual reference orientation of the wearable device.

29. The method of claim 20, further comprising:
identifying that at least a portion of the wearable device has moved on the wrist or forearm of the user; and
determining the current position and/or orientation of the wearable device on the user in response to identifying that at least a portion of the wearable device has moved on the wrist or forearm of the user.

30. The method of claim 29, wherein identifying the at least a portion of the wearable device has moved on the wrist or forearm of the user comprises determining that the wearable device has rotated around and/or translated along the user's wrist or forearm.

31. The method of claim 29, wherein identifying the at least a portion of the wearable device has moved on the wrist or forearm of the user comprises detecting one or more movement artifacts in the sensed plurality of neuromuscular signals.

32. The method of claim 29, further comprising identifying the at least a portion of the wearable device has moved on the wrist or forearm of the user is based, at least in part, on at least one signal sensed by at least one inertial measurement unit (IMU) sensor.

33. A method comprising:
receiving neuromuscular signals sensed from body parts of a plurality of users as a wearable device was worn by each of the users while performing a plurality of hand gestures and/or poses, wherein for each of the plurality of hand gestures and/or poses, the wearable device was oriented or positioned differently on the user, and wherein the wearable device includes a plurality of sensors including one or more electrodes arranged in a specified order;
labeling the received neuromuscular signals for each of the plurality of hand gestures and/or poses based on the orientation or position of the wearable device during sensing of the corresponding neuromuscular signals, wherein sensing the neuromuscular signals includes:
defining a virtual reference electrode among the electrodes of the wearable device; and determining a rotation offset relative to the virtual reference electrode; and determining a current position of the wearable device on the user, wherein the orientation is established at least partially based on the determined rotation offset value relative to the virtual reference electrode, and wherein the trained autocalibration models are configured to align the rotation, location, and orientation of the wearable device via reference points that represent the same portion of the body part of the user irrespective of the wearable device's position on that body part, the aligning further including:

applying, by the processor, an electrode permutation that alters the order of the electrodes according to the orientation of the wearable device relative to the user's body part; and applying, by the processor, a circular rotation to the electrodes to adapt to detected rotational changes in the plurality of sensors;

training one or more autocalibration models based, at least in part, on the labeled neuromuscular signals; and generating a control signal based, at least in part, on the current position and/or orientation of the wearable device on the user and the plurality of neuromuscular signals, wherein the control signal instructs the user to perform a specified action based on the determined current position of the plurality of sensors.

34. The method of claim 33, further comprising:

extracting from the received neuromuscular signals, a plurality of templates, where each of the plurality of templates corresponds to one of the plurality of hand gestures and/or poses; and generating calibrated neuromuscular signals based, at least on the extracted plurality of templates, and wherein training the one or more autocalibration models comprises training the one or more autocalibration models based, at least in part, on the calibrated neuromuscular signals.

35. The method of claim 33, further comprising:

predicting a plurality of rotation offsets of the wearable device using a plurality of simulations of different orientations.

36. The method of claim 33, wherein the one or more autocalibration models include a neural network.

37. The method of claim 36, wherein the neural network is an LSTM neural network.

\* \* \* \* \*